US007846891B2

(12) United States Patent
Ellis-Behnke et al.

(10) Patent No.: US 7,846,891 B2
(45) Date of Patent: Dec. 7, 2010

(54) SELF-ASSEMBLING PEPTIDES FOR REGENERATION AND REPAIR OF NEURAL TISSUE

(75) Inventors: Rutledge Ellis-Behnke, Canton, MA (US); Gerald Schneider, Somerville, MA (US); Shuguang Zhang, Lexington, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 95 days.

(21) Appl. No.: 10/968,790

(22) Filed: Oct. 18, 2004

(65) Prior Publication Data
US 2005/0287186 A1 Dec. 29, 2005

Related U.S. Application Data

(60) Provisional application No. 60/512,510, filed on Oct. 17, 2003.

(51) Int. Cl.
C07K 14/00 (2006.01)
A61K 38/00 (2006.01)
C07H 21/04 (2006.01)

(52) U.S. Cl. .......................... 514/2; 530/300; 536/23.1; 536/24.1

(58) Field of Classification Search ........................ None
See application file for complete search history.

(56) References Cited

U.S. PATENT DOCUMENTS 5,955,343 A * 9/1999 Holmes et al. ............... 435/325
7,098,028 B2 * 8/2006 Holmes et al. ............... 435/401

OTHER PUBLICATIONS

Novikova et al., "Biopolymers and biodegradable smart implants for tissue regeneration after spinal cord injury", Current Opinion in Neurology 16: 711-715 (2003).*
Buffo et al.,"Targeted overexpression of the neurite growth-associated protein B-50/GAP-43 in cerebellar Purkinje cells induces sprouting after axotomy but not axon regeneration into growth-permissive transplants", The Journal of Neuroscience 17(22): 8778-8791 (1997).*
Sakaguchi et al., "Transplantation of neural progenitor cells into the developing retina of the Brazilian opossum: an in vivo system for studying stem/progenitor cell plasticity", Dev Neurosci 26: 336-345 (2004).*
Yang et al., "Differential lineage restriction of rat retinal progenitor cells in vitro and in vivo", Journal of Neuroscience Research 69: 466-476 (2002).*
Aguayo, et al., "Growth and Connectivity of Axotomized Retinal Neurons in Adult Rats with Optic Nerves Substituted by PNS Grafts Linking the Eye and the Midbrain" *Acad Sci.* 495: 1-9, 1987.
Aguayo, et al., "Regrowth and Connectivity of Injured Central Nervous System Axons in Adult Rodents." *Acta Neurobiol Exp.* 50(4-5): 381-9, 1990.
Aguayo, et al., "Effects of Neurotrophins on the Survival and Regrowth of Injured Retinal Neurons." *Ciba Found Symp,* 196: 135-44, 1996.
Aleksandrova, et al., "Effect of the Foreign Gene GDNF on Development of Homo-and Xenografts in the Rat Brain." *Genetika* 36(11): 1553-60, 2000.
Archiblad, et al., "Monkey Median Nerve Repaired by Nerve Graft or Collagen Nerve Guide Tube" *J Neurosci* 15(5): 4109-4123, 1995.
Arutiunov, et al., "Plastic Repair of Defects in the Dura Mater" *Vopr Neirokhir* 36(3): 3-9, 1972.
Bernstein, et al., "Effects of Puromycin Treatment on the Regeneration of Hemisected and Transected Rat Spinal Cord" *J Neurocytol* 7(2): 215-28, 1978.
Bernstein, et al., "Functional and Cellular Responses in a Novel Rodent Model of Anterior Ischemic Optic Neuropathy" *Invest Ophthalmol Vis Sci* 44(10): 4153-62, 2003.
Bjorklund, et al., "Neural Transplantation for the Treatment of Parkinson's Disease" *Lancet Neurol* 2(7): 437-45, 2003.
Bromze, et al., "Spinal Axon Regeneration Evoked by Replacing Two Growth Cone Proteins in Adult Neurons." *Nat Neurosci* 4(1): 38-43, 2001.
Brummelkamp, et al., "A System for Stable Expression of Short Interfering RNAs in Mammalian Cells" *Science* 296: 550-553, 2002.
Caplan, et al., "Self-Assembly of a Beta-Sheet Protein Governed by Relief of Electrostatic Repulsion Relative to Van Per Waals Attraction." *Biomacromolecules* 1(4): 627-31, 2000.
Caplan, et al., "Control of Self-Assembling Oligopeptide Matrix Formation Through Systematic Variation of Amino Acid Sequence." *Biomaterials* 23: 219-227, 2002.
Caplan, et al., "Effects of Systematic Variation of Amino Acid Sequence on the Mechanical Properties of a Self-Assembling, Oligopeptide Biomaterial" *J Biomater Sci Polymer Edition* 13: 225-236, 2002.

(Continued)

*Primary Examiner*—Anand U Desai
(74) *Attorney, Agent, or Firm*—Choate, Hall & Stewart; Jeffrey E. Buchholz

(57) ABSTRACT

The present invention provides methods and compositions for enhancing regeneration and/or repair of neural tissue. One method include providing a nanoscale structured material at the site of injury, wherein the nanoscale structured material provides an environment that is permissive for regeneration of neural tissue and allows axon growth from a location on one side of a site of injury or barrier to a location on the other side of the site of injury or barrier. A second method includes introducing a composition comprising self-assembling peptides into the subject at the site of injury, wherein the peptides are amphiphilic peptides that comprise substantially equal proportions of hydrophobic and hydrophilic amino acids and are complementary and structurally compatible. A variety of compositions comprising a nanoscale structured material or precursor thereof, and an additional substance such as a regeneration promoting factor, are also provided. In certain embodiments of the invention the nanoscale structured material or precursor thereof comprises self-assembling peptides. The invention further provides compositions and methods for repair of an intervertebral disc, including nucleus pulpusos repair.

10 Claims, 13 Drawing Sheets

OTHER PUBLICATIONS

Carter, et al., "Regenerated Retinal Ganglion Cell Axons Form Normal Numbers of Boutons But Fail to Expand Their Arbors in the Superior Colliculus" *J Neurocytol* 27(3): 187-96, 1998.

Carter, et al., "Regenerated Retinal Ganglion Cell Axons Can Form Well-Differentiated Synapses in the Superior Colliculus of Adult Hamsters." *J Neurosci* 9(11): 4042-50, 1989.

Chen, et al., "Bcl-2 Promotes Regeneration of Several Axons in Mammalian CNS" *Nature* 385(6615): 434-9, 1997.

Chen, et al., "Intrinsic Changes in Developing Retinal Neurons Result in Regenerative Failure of Their Axons" *Proc Natl Acad Sci USA* 92(16): 7287-91, 1995.

Chen, et al., "Long Term Lithium Treatment Suppresses p53 and Bax Expression but Increases Bcl-2 Expression. A Prominent Role in Neuroprotection Against Excitotoxicity." *J Biol Chem* 274(10): 6039-42, 1999.

Cho, et al., "Ciliary Neurotrophic Factor Promotes the Regrowth Capacity But not the Survival of Intraorbitally Axotomized Retinal Ganglion Cells in Adult Hamsters." *Neuroscience* 94(2): 623-8, 2000.

Cohen, et al., "Neurotrophin-4/5 (NT-4/5) Increases Adult Rat Retinal Ganglion Cell Survival and Neurite Outgrowth in Vitro." *J Neurobiol* 25(8): 953-9, 1994.

Del Rio, et al., "Proliferation and Differentiation of Glial Fibrillary Acidic Protein-Immunoreactive Glial Cells in Organotypic Slice Cultures of Rat Hippocampus" *Neuroscience* 43(2-3): 335-47, 1991.

DeVivo, et al., "Epidemiology of Traumatic Spinal Cord Injury" *Spinal Cord Medicine* 69-81, 2002.

Ellis-Behnke, et al., "In Vitro Assay of CNS Regeneration Through Lesion Scars Produced In-Vivo, With Treatments to Increase Growth" *Society for Neuroscience* 2002.

Ellis-Behnke, et al., "A Method for Non-Viral Genetic Transfection in the CNS, Using Bcl-2 In-Vivo" *Society for Neuroscience*, 27: 2001.

Esser, et al., "CD95(Fas/APO-1) Antibody-Mediated Apoptosis of Human Retinal Pigment Epithelial Cells" *Biochem Biophys Res Commun* 213(3): 1026-34, 1995.

Fukuda, et al., "Functional Recovery of Vision in Regenerated Optic Nerve Fibers" *Vision Res.* 38(10): 1545-53, 1998.

Han, et al., "Development of Biomaterial for Gene Therapy" *Mol. Therapy* 2: 302-317, 2000.

Heiduschka, et al., "Aurintricarboxylic Acid Promotes Survival and Regeneration of Axomised Retinal Ganglion Cells in Vivo" *Nueropharmacology* 39(5): 889-902, 2000.

Holmes, et al., Extensive Neurite Outgrowth and Active Synapse Formation on Self-Assembling Peptide Scaffolds. *Proc Natl Acad Sci USA* 97(12): 6728-33, 2000.

Huang-Lee, et al., "Effects of Hyaluronan on Collagen Fibrillar Matrix Contraction by Fibroblasts." *J Biomed Mater Res* 28(1): 123-32, 1994.

Jiang, et al., "Fas Mediates Apoptosis and Oxidant-Induced Cell Death in Cultured hRPE Cells" *Invest Ophthalmol Vis Sci* 41(3): 645-55, 2000.

Kaplan, et al., "Fas Ligand (CD95 Ligand) Controls Angiogenesis Beneath the Retina" *Nat Med* 5(3): 292-7, 1999.

Keirstead, et al., "Responses to Light of Retinal Neurons Regenerating Axons into Peripheral Nerve Grafts in the Rat" *Brain Res* 359(1-2): 402-6, 1985.

Keirstead, et al., "Electrophysiologic Responses in Hamster Superior Colliculus Evoked by Regenerating Retinal Axons" *Science* 246(4927): 255-7, 1989.

Khodzhaev, et al., "Healing of Meningo-Cerebral Wounds with a Combination of Plastic Repair and Hydrocortisone Therapy Under Clinical and Experimental Conditions." *Vopr Neirokhir* 4: 35-7, 1976.

Kisiday, et al., "Self-Assembling Peptide Hydrogel Fosters Chondrocyte Extracellular Matrix Production and Cell Division: Implications for Cartilage Tissue Repair" *Proc. Natl. Acad. USA* 99: 9996-10001, 2002.

Kitchigina, et al., "Functional Integration of the Rat Hippocampal Tissue, Transplanted into the Rabbit Septum." Brain Res 502(1): 39-52, 1989.

Korochkin, et al., "New Approaches in Developmental Genetics and Gene Therapy: Xenotransplantation of Drosophila Embryonic Nerve Cells into the Brain of Vertebrate Animals." *Genetika* 36(11): 1436-42, 2000.

Kotzbauer, et al., "Neurturin, A Relative of Glial-Cell-Line-Derived Neurotrophic Factor." *Nature* 384(6608): 467-70, 1996.

Krueger, et al., "Protocol of Thromboembolic Stroke Model in the Rat: Review of the Experimental Procedure and Comparison of Models." *Invest Radiol* 37(11): 600-8, 2002.

Lambooij, et al., "Apoptosis is Present in the Primate Macula at All Ages." *Graefes Arch Clin Exp Ophthalmol* 238(6): 508-14, 2000.

Larsson, et al., "Intrastriatal Ventral Mesencephalic Xenografts of Porcine Tissue in Rats: Immune Responses and Functional Effects." *Cell Transplant* 9(2): 261-72, 2000.

Lendahl, et al., "CNS Stem Cells Express a New Class of Intermediate Filament Protein" *Cell* 60: 585-595, 1990.

Leon, et al., "Mechanical Properties of a Self-Assembling Oligopeptide Matrix." *J. Biomater Sci Polym Ed* 9(3): 297-312, 1998.

Ling, et al., "Target-Specific Morphology of Retinal Axon Arbors in the Adult Hamster" *Vis Neurosci* 15(3): 559-79, 1998.

Lundborg, et al., "Nerve Regeneration Model and Trophic Factors In Vivo." *Brain Res.* 232(1): 157-61, 1982.

Manji, et al., Lithium at 50: Have the Neuroprotective Effects of This Unique Cation Been Overlooked? *Biol Psychiatry* 46(7): 929-40, 1999.

Manji, et al., "Lithium Up-Regulates the Cytoprotective Protein Bcl-2 in the CNS in Vivo: A Role for Neurotrophic and Neuroprotective Effects in Manic Depressive Illness." *J Clin Psychiatry* 61(9): 82-96, 2000.

Mansour-Robaey, et al., "Effects of Ocular Injury and Administration of Brain-Derived Neurotrophic Factor on Survival and Regrowth of Axotomized Retinal Ganglion Cells." *Proc Natl Acad Sci USA* 91(5): 1632-6, 1994.

Mao, et al., "A Nanomechanical Device Based on the B-Z Transition of DNA." *Nature* 397(6715): 144-6, 1999.

McCaffrey, et al., "Inhibition of Hepatitis B Virus in Mice by RNA Interference." *Nat Biotechnol* 21: 639-644, 2003.

McManus, et al., "Gene Silencing in Mammals by Short Interfering RNAs" *Nature Rev Gene* 3: 737-747, 2002.

Mikkelsen, et al., "Visualization of Efferent Retinal Projections by Immmunohistochemical Identification of Cholera Toxin Subunit B" *Brain Res Bull* 28(4): 619-23, 1992.

Moore, et al., "Lithium Increases N-Acetyle-Aspartate in the Human Brain: In Vivo Evidence in Support of BCL-2's Neurotrophic Effects?" *Biol Psychiatry* 48(1): 1-8, 2000.

Munter, et al., "Trends in Stroke Prevalence Between 1973 and 1991 in the US Population 27 to 74 years of Age" *Stroke* 33: 1209-1213, 2002.

Nakashima, et al., "Immunological Reaction and Blood-Brain Barrier in Mouse-to-Rat Cross-Species Neural Graft." *Brain Res.* 475(2): 232-43, 1988.

Paddison, et al., "Short Hairpin RNAs (shRNAs) Induce Sequence-Specific Silencing in Mammalian Cells." *Genes Dev* 16: 948-958, 2002.

Plant, et al., "Axonal Growth Within Poly (2-Hydroxyethyl Methacrylate) Sponges Infiltrated with Schwann Cells and Implanted into the Lesioned Rat Optic Tract." *Brain Res* 671(1): 119-30, 1995.

Reinhardt, et al., "Mapping of Nidogen Binding Sites for Collagen Type IV, Heparan Sulfate Proteoglycan and Zinc" *J Biol Chem* 268(15): 10881-7, 1993.

Remy, et al., "Different Mechanisms Mediate the Rejection of Porcine Neurons and Endothelial Cells Transplanted into the Rat Brain" *Xenotransplantation* 8(2): 136-48, 2001.

Rende, et al., Immunolocalization of Ciliary Neuronotrophic Factor in Adult Rat Sciatic Nerve. *Glia* 5(1): 25-32, 1992.

Rosenblat, et al., "Acylated Ascorbate Stimulates Collagen Synthesis in Cultured Human Foreskin Fibroblasts at Lower Doses Than Does Ascorbic Acid" *Connect Tissue Res* 37(3-4): 303-11, 1998.

Saarma, et al., "Other Neurotrophic Factors: Glial Cell Line-Derived Neurotrophic Factor (GDFN)" *Microsc Res Tech* 45(4-5): 292-302, 1999.

Sasaki, et al., "Light-dark Discrimination after Sciatic Nerve Transplantation to the Sectioned Optic Nerve in Adult Hamsters." *Vision Res* 33(7): 877-80, 1993.

Sawai, et al., "Functional and Morphological Restoration of Intracranial Brachial Lesion of the Retinocollicular Pathway by Peripheral Nerve Autografts in Adult Hamsters" Exp Neurol 137(1): 94-104, 1996.

Schmidt, et al., Neural Tissue Engineering: Strategies for Repair and Regeneration *Annu. Rev. Biomed. Eng.* 5: 293-347, 2003.

Schneider, et al., "Visual Function Due to Regeneration of Optic Nerve or Optic Tract Through Peripheral Nerve Homografts" *Soc. Neurosci* 26: 611, 2000.

Schneider, et al., "Is it Really Better to Have Your Brain Lesion Early? A Revision of the 'Kennard Principle'" *Neuropsychologia* 17(6): 557-83, 1979.

Snow, et al., "Sulfated Proteoglycans in Astroglial Barriers Inhibit Neurite Outgrowth in Vitro" *Exp Neurol* 109(1): 111-30, 1990.

Snow, et al., "A Chondroitin Sulfate Proteoglycan May Influence the Direction of Retinal Ganglion Cell Outgrowth." *Development* 113(4): 1473-85, 1991.

So, et al., "Lesions of Brachium of the Superior Colliculus in Neonate Hamsters: Correlation of Anatomy with Behavior" *Exp. Neurol* 72(2): 379-400, 1981.

So, et al., "Lengthy Regrowth of Cut Axons from Ganglion Cells After Peripheral Never Transplantation into the Retina of Adult Rats" *Brain Res.* 382(2): 349-54, 1985.

Stichel, et al., "Inhibition of Collagen IV Deposition Promotes Regeneration of Injured CNS Axons." *Eur J Neurosci* 11(2): 632-46, 1999.

Stoppini, et al., "A Simple Method for Organotypic Cultures of Nervous Tissue" *JNeurosci Methods* 37(2): 173-82, 1991.

Suave, et al., "Functional Synaptic Connections Made by Regenerated Retinal Ganglion Cell Axons in the Superior Colliculus of Adult Hamsters" *J Neurosci* 15(1 Pt2): 665-75, 1995.

Suave, et al., "Topological Specificity in Reinnervation of the Superior Colliculus by Regenerated Retinal Ganglion Cell Axons in Adult Hamsters" *J Neurosci.* 21(3): 951-960, 2001.

Teng, et al., "Functional Recovery Following Traumatic Spinal Cord Injury Mediated by a Unique Polymer Scaffold Seeded with Neural Stem Cells." *Proc Natl Acad Sci USA* 99(5): 3024-9, 2002.

Thanos, et al., "Type-Specific Stabilization and Target-Dependent Survival of Regenerating Ganglion Cells in the Retina of Adult Rats" *J Neurosci.* 15(2): 1057-79, 1995.

Thanos, et al., "Regenerating Ganglion Cell Axons in the Adult Rat Establish Retinofugal Topography and Restore Visual Function" *Exp. Brain Res.* 114(3): 483-491, 1997.

Thomas, et al., "Non-viral Gene Therapy: Polycation-Mediated DNA Delivery. Appl. Microbiol. Biotechnol." 62: 27-34, 2003.

Varon, et al., "Trophic Mechanisms in the Peripheral Nervous System." *Annu Rev Neurosci* 1: 327-61, 1978.

Varon, et al., "Trophic Activities for Dorsal Root and Sympathetic Ganglionic Neurons in Media Conditioned by Schwann and other Peripheral Cells." *Brain Res* 227(1): 73-87, 1981.

Villegas-Perez, et al., "Influences on Peripheral Nerve Grafts on the Survival and Regrowth of Axotomized Retinal Ganglion Cells in Adult Rats." *J Neurosci* 8(1): 265-80, 1988.

Vogel, et al., "The Role of Glycolipids in Mediating Cell Adhesion: A Flow Chamber Study" Biochim Biophys Acta 1372(2): 205-15, 1998.

Yick, et al., "Peripheral Never Graft and Neurotrophic Factors Enhance Neuronal Survival and Expression of Nitric Oxide Synthase in Clarke's Nucleus after Hemisection of the Spinal Cord in Adult Rat." *Exp Neurol* 159(1): 131-8, 1999.

Yip, et al., "Axonal Regeneration of Retinal Ganglion Cells: Effect of Trophic Factors" *Prog Retin Eye Res* 19(5): 559-75, 2000.

Zhang, et al., "Spontaneous Assembly of a Self-Complementary Oligopeptide to Form a Stable Macroscopic Membrane" *Proc Natl Acad Sci USA* 90(8): 3334-8, 1993.

Zhang, et al., "Self-Complementary Oligopeptide Matrices Support Mammalian Cell Attachment" *Biomaterials* 16(18): 1385-93, 1995.

Zhang, et al., "Zuotin, A Putative Z-DNA Binding Protein in *Saccharomyces cerevisiae*" Embo J. 11(10): 3787-96, 1992.

Zhang, et al., "Emerging Biological Materials Through Molecular Self-Assembly." *Biotechnology Advances* 20: 321-339, 2002.

Zhang, et al., "Biological Surface Engineering: A Simple System for Cell Pattern Formation" *Biomaterials* 20(13): 1213-20, 1999.

* cited by examiner

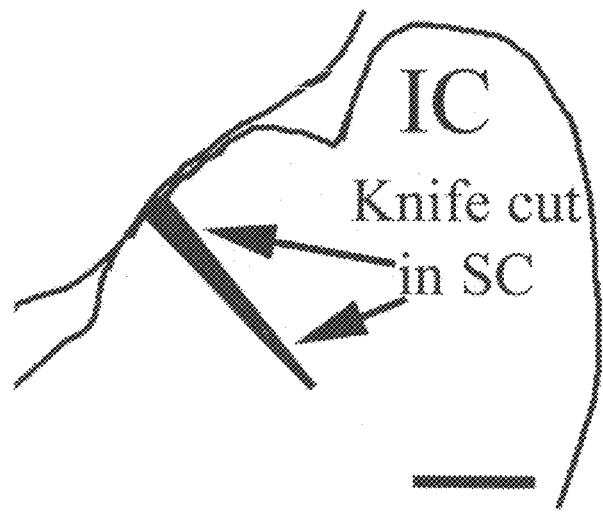
Figure: 2
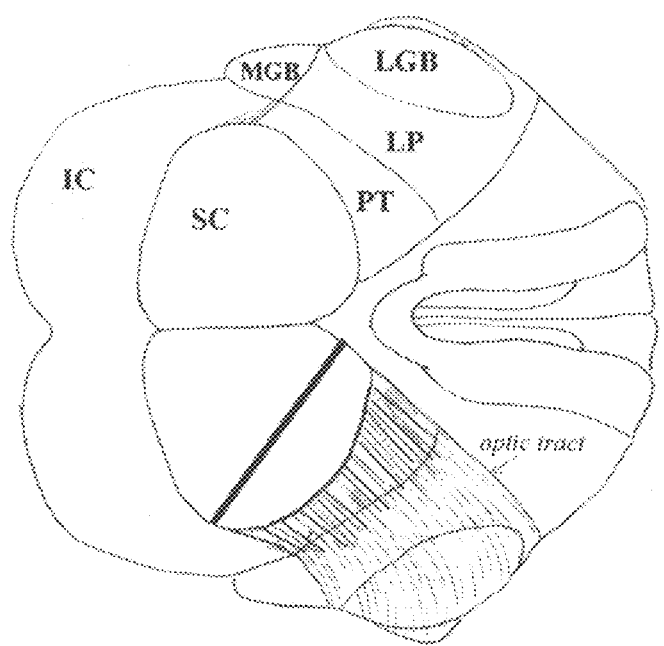
Figure 3

Heavy line curving across Optic Tract = Lesion of brachium of SC (superior colliculus)
IC = inferior colliculus, LGB = lateral geniculate body, LP = lateral posterior nucleus,
MGB = medial geniculate body, PT = pretectal area.

SEQUENCE LISTING

<160> NUMBER OF SEQ ID NOS: 31

<210> SEQ ID NO 1
<211> LENGTH: 16
<212> TYPE: DNA
<213> ORGANISM: Artificial Sequence
<220> FEATURE:
<223> OTHER INFORMATION: Self-Assembling Peptides

<400> SEQUENCE: 1
radaradara darada                                                  16

<210> SEQ ID NO 2
<211> LENGTH: 16
<212> TYPE: DNA
<213> ORGANISM: Artificial Sequence
<220> FEATURE:
<223> OTHER INFORMATION: Self-Assembling Peptides

<400> SEQUENCE: 2
radargdara dargda                                                  16

<210> SEQ ID NO 3
<211> LENGTH: 8
<212> TYPE: DNA
<213> ORGANISM: Artificial Sequence
<220> FEATURE:
<223> OTHER INFORMATION: Self-Assembling Peptides

<400> SEQUENCE: 3

```
radarada                                                    8

<210> SEQ ID NO 4
<211> LENGTH: 16
<212> TYPE: DNA
<213> ORGANISM: Artificial Sequence
<220> FEATURE:
<223> OTHER INFORMATION: Self-Assembling Peptides

<400> SEQUENCE: 4
raradadara radada                                          16

<210> SEQ ID NO 5
<211> LENGTH: 8
<212> TYPE: DNA
<213> ORGANISM: Artificial Sequence
<220> FEATURE:
<223> OTHER INFORMATION: Self-Assembling Peptides

<400> SEQUENCE: 5 raradada                                                    8

<210> SEQ ID NO 6
<211> LENGTH: 16
<212> TYPE: PRT
<213> ORGANISM: Artificial Sequence
<220> FEATURE:
<223> OTHER INFORMATION: Self-Assembling Peptides

<400> SEQUENCE: 6

Ala Glu Ala Lys Ala Glu Ala Lys Ala Glu Ala Lys Ala Glu Ala Lys
1               5                   10                  15

<210> SEQ ID NO 7
<211> LENGTH: 8
<212> TYPE: PRT
<213> ORGANISM: Artificial Sequence
<220> FEATURE:
<223> OTHER INFORMATION: Self-Assembling Peptides

<400> SEQUENCE: 7

Ala Glu Ala Lys Ala Glu Ala Lys
1               5

<210> SEQ ID NO 8
<211> LENGTH: 16
<212> TYPE: PRT
<213> ORGANISM: Artificial Sequence
<220> FEATURE:
<223> OTHER INFORMATION: Self-Assembling Peptides

<400> SEQUENCE: 8

Arg Ala Glu Ala Arg Ala Glu Ala Arg Ala Glu Ala Arg Ala Glu Ala
1               5                   10                  15

<210> SEQ ID NO 9
<211> LENGTH: 8
<212> TYPE: PRT
<213> ORGANISM: Artificial Sequence
<220> FEATURE:
<223> OTHER INFORMATION: Self-Assembling Peptides

<400> SEQUENCE: 9

Arg Ala Glu Ala Arg Ala Glu Ala
1               5
```

```
<210> SEQ ID NO 10
<211> LENGTH: 16
<212> TYPE: DNA
<213> ORGANISM: Artificial Sequence
<220> FEATURE:
<223> OTHER INFORMATION: Self-Assembling Peptides

<400> SEQUENCE: 10
kadakadaka dakada                                                    16

<210> SEQ ID NO 11
<211> LENGTH: 8
<212> TYPE: DNA
<213> ORGANISM: Artificial Sequence
<220> FEATURE:
<223> OTHER INFORMATION: Self-Assembling Peptides

<400> SEQUENCE: 11 kadakada                                                              8

<210> SEQ ID NO 12
<211> LENGTH: 17
<212> TYPE: PRT
<213> ORGANISM: Artificial Sequence
<220> FEATURE:
<223> OTHER INFORMATION: Self-Assembling Peptides

<400> SEQUENCE: 12

Ala Glu Ala Glu Ala Glu His Ala His Ala Glu Ala Glu Ala His Ala
1               5                   10                  15

His

<210> SEQ ID NO 13
<211> LENGTH: 8
<212> TYPE: PRT
<213> ORGANISM: Artificial Sequence
<220> FEATURE:
<223> OTHER INFORMATION: Self-Assembling Peptides

<400> SEQUENCE: 13

Ala Glu Ala Glu Ala His Ala His
1               5

<210> SEQ ID NO 14
<211> LENGTH: 16
<212> TYPE: PRT
<213> ORGANISM: Artificial Sequence
<220> FEATURE:
<223> OTHER INFORMATION: Self-Assembling Peptides

<400> SEQUENCE: 14

Phe Glu Phe Glu Phe Lys Phe Lys Phe Glu Phe Glu Phe Lys Phe Lys
1               5                   10                  15

<210> SEQ ID NO 15
<211> LENGTH: 8
<212> TYPE: PRT
<213> ORGANISM: Artificial Sequence
<220> FEATURE:
<223> OTHER INFORMATION: Self-Assembling Peptides

<400> SEQUENCE: 15

Phe Glu Phe Lys Phe Glu Phe Lys
1               5
```

```
<210> SEQ ID NO 16
<211> LENGTH: 16
<212> TYPE: PRT
<213> ORGANISM: Artificial Sequence
<220> FEATURE:
<223> OTHER INFORMATION: Self-Assembling Peptides

<400> SEQUENCE: 16

Leu Glu Leu Glu Leu Lys Leu Lys Leu Glu Leu Glu Leu Lys Leu Lys
1               5                   10                  15

<210> SEQ ID NO 17
<211> LENGTH: 8
<212> TYPE: PRT
<213> ORGANISM: Artificial Sequence
<220> FEATURE:
<223> OTHER INFORMATION: Self-Assembling Peptides

<400> SEQUENCE: 17

Leu Glu Leu Glu Leu Lys Leu Lys
1               5

<210> SEQ ID NO 18
<211> LENGTH: 16
<212> TYPE: PRT
<213> ORGANISM: Artificial Sequence
<220> FEATURE:
<223> OTHER INFORMATION: Self-Assembling Peptides

<400> SEQUENCE: 18

Ala Glu Ala Glu Ala Lys Ala Lys Ala Glu Ala Glu Ala Lys Ala Lys
1               5                   10                  15

<210> SEQ ID NO 19
<211> LENGTH: 12
<212> TYPE: PRT
<213> ORGANISM: Artificial Sequence
<220> FEATURE:
<223> OTHER INFORMATION: Self-Assembling Peptides

<400> SEQUENCE: 19

Ala Glu Ala Glu Ala Glu Ala Glu Ala Lys Ala Lys
1               5                   10

<210> SEQ ID NO 20
<211> LENGTH: 8
<212> TYPE: PRT
<213> ORGANISM: Artificial Sequence
<220> FEATURE:
<223> OTHER INFORMATION: Self-Assembling Peptides

<400> SEQUENCE: 20

Ala Glu Ala Glu Ala Lys Ala Lys
1               5

<210> SEQ ID NO 21
<211> LENGTH: 16
<212> TYPE: PRT
<213> ORGANISM: Artificial Sequence
<220> FEATURE:
<223> OTHER INFORMATION: Self-Assembling Peptides

<400> SEQUENCE: 21

Lys Ala Lys Ala Lys Ala Lys Ala Glu Ala Glu Ala Glu Ala Glu Ala
1               5                   10                  15

<210> SEQ ID NO 22
```

```
<211> LENGTH: 16
<212> TYPE: PRT
<213> ORGANISM: Artificial Sequence
<220> FEATURE:
<223> OTHER INFORMATION: Self-Assembling Peptides

<400> SEQUENCE: 22

Ala Glu Ala Glu Ala Glu Ala Glu Ala Lys Ala Lys Ala Lys Ala Lys
1               5                   10                  15

<210> SEQ ID NO 23
<211> LENGTH: 16
<212> TYPE: DNA
<213> ORGANISM: Artificial Sequence
<220> FEATURE:
<223> OTHER INFORMATION: Self-Assembling Peptides

<400> SEQUENCE: 23
rarararada dadada                                                        16

<210> SEQ ID NO 24
<211> LENGTH: 16
<212> TYPE: DNA
<213> ORGANISM: Artificial Sequence
<220> FEATURE:
<223> OTHER INFORMATION: Self-Assembling Peptides

<400> SEQUENCE: 24
adadadadar ararar                                                        16

<210> SEQ ID NO 25
<211> LENGTH: 16
<212> TYPE: DNA
<213> ORGANISM: Artificial Sequence
<220> FEATURE:
<223> OTHER INFORMATION: Self-Assembling Peptides

<400> SEQUENCE: 25
dadadadara rarara                                                        16

<210> SEQ ID NO 26
<211> LENGTH: 16
<212> TYPE: DNA
<213> ORGANISM: Artificial Sequence
<220> FEATURE:
<223> OTHER INFORMATION: Self-Assembling Peptides

<400> SEQUENCE: 26
adadadadar ararar                                                        16

<210> SEQ ID NO 27
<211> LENGTH: 16
<212> TYPE: PRT
<213> ORGANISM: Artificial Sequence
<220> FEATURE:
<223> OTHER INFORMATION: Self-Assembling Peptides

<400> SEQUENCE: 27

His Glu His Glu His Lys His Lys His Glu His Glu His Lys His Lys
1               5                   10                  15

<210> SEQ ID NO 28
<211> LENGTH: 8
<212> TYPE: PRT
<213> ORGANISM: Artificial Sequence
<220> FEATURE:
<223> OTHER INFORMATION: Self-Assembling Peptides
```

```
<400> SEQUENCE: 28

His Glu His Glu His Lys His Lys
1               5

<210> SEQ ID NO 29
<211> LENGTH: 20
<212> TYPE: PRT
<213> ORGANISM: Artificial Sequence
<220> FEATURE:
<223> OTHER INFORMATION: Self-Assembling Peptides

<400> SEQUENCE: 29

Val Glu Val Glu Val Glu Val Glu Val Glu Val Glu Val Glu Val Glu
1               5                   10                  15

Val Glu Val Glu
            20

<210> SEQ ID NO 30
<211> LENGTH: 20
<212> TYPE: PRT
<213> ORGANISM: Artificial Sequence
<220> FEATURE:
<223> OTHER INFORMATION: Self-Assembling Peptides

<400> SEQUENCE: 30

Arg Phe Arg Phe Arg Phe Arg Phe Arg Phe Arg Phe Arg Phe Arg Phe
1               5                   10                  15

Arg Phe Arg Phe
            20

<210> SEQ ID NO 31
<211> LENGTH: 4
<212> TYPE: PRT
<213> ORGANISM: Artificial Sequence
<220> FEATURE:
<223> OTHER INFORMATION: Self-Assembling Peptides

<400> SEQUENCE: 31

Arg Ala Asp Ala
1
```

SELF-ASSEMBLING PEPTIDES FOR REGENERATION AND REPAIR OF NEURAL TISSUE

CROSS-REFERENCE TO RELATED APPLICATION

This application claims priority to U.S. Provisional Patent Application 60/512,510, filed Oct. 17, 2003, which is incorporated herein by reference.

GOVERNMENT SUPPORT

The United States Government has provided grant support utilized in the development of the present invention. In particular, National Institutes of Health grant number EY00126 has supported development of this invention. The United States Government may have certain rights in the invention.

BACKGROUND OF THE INVENTION

While soft tissues (e.g., muscle and skin) and bone possess considerable capacity for recovery after injury, inadequate nerve repair frequently limits the extent to which normal function is regained. In the peripheral nervous system (PNS), nerves are often able to regenerate on their own, if the injury is small enough. Larger injuries may be effectively treated surgically, either by direct reconnection of damaged nerve ends with the nerve sheath the axons previously used to reach their destination or with grafts harvested from elsewhere in the body. However, clinical functional recovery rates generally approach only 80% following nerve graft, and the procedure has the additional disadvantage of requiring two surgeries. An alternative approach to nerve repair in the PNS is to provide an artificial conduit, such as the NeuraGen™ Nerve Guide (Integra LifeSciences, Plainsboro, N.J.), a collagen tube providing a conduit for axonal growth across a nerve gap [83]. However, this treatment is typically reserved for small defects (e.g., several millimeters).

Clinical treatment of injuries to the central nervous system (CNS) is considerably less successful. Unlike nerves in the PNS, axons in the CNS do not undergo significant regeneration in their native environment. Thus initial therapy is usually limited to removal of bone fragments to prevent secondary injury and administration of drugs such as corticosteroids to reduce swelling. Currently there is no effective treatment available to completely restore nerve function in the CNS. Rehabilitation, in which patients train remaining nerves to compensate for loss due to injury, remains the mainstay of therapy.

Despite the relatively bleak outlook for regeneration of injured nerves in the CNS, advances in other areas of medical care have greatly improved the rate of survival of patients with traumatic CNS injuries, e.g., traumatic injury to the spinal cord. Nearly 94% of patients with spinal cord injuries survive the first year following injury, and of these, 93% are able to be discharged back into the community [84]. Approximately 10,000-12,000 individuals suffer spinal cord injuries each year in the United States, bringing the projected prevalence rate in the United States to nearly 280,000 by the year 2014 [84].

The number of patients with traumatic spinal cord or brain injury is dwarfed by the number of persons who experience damage to the CNS due to diseases and stroke [85], or as a consequence of conditions such as primary brain tumors, brain metastastes from tumors elsewhere in the body, or surgery for these conditions. Survivors of stroke and survivors of brain lesions due to tumors or surgical damage frequently experience permanent deficits in function due to loss of brain tissue either as a direct consequence of injury or secondary to events such as swelling and/or release of neurotoxic substances from necrotic tissue. While emerging therapies for these patients may offer the potential to limit such damage, prospects for restoring function lost due to death of brain cells and disruption of brain architecture remain poor, and therapeutic efforts focus on rehabilitation.

It is therefore evident that a significant need in the art exists for improved treatments that would enhance repair and regeneration in the CNS. In addition, there remains a need in the art for improved treatments that would enhance nerve repair and regeneration in the PNS since current treatments, while frequently effective, have a number of disadvantages.

SUMMARY OF THE INVENTION

The present invention addresses these needs, among others. In one aspect, the invention provides a method for enhancing repair or regeneration of neural tissue at a site of injury in a mammalian subject comprising: providing a nanoscale structured material, or a precursor thereof, at the site of injury, wherein the nanoscale structured material provides an environment that is permissive for regeneration of neural tissue and allows axon growth from one side of a site of injury or barrier to the other side of the site of injury or barrier. In certain embodiments of the invention the step of providing comprises introducing a composition comprising a precursor of the nanoscale structured material at or in the vicinity of the site of injury, wherein the precursor assembles in situ to form the nanscale structured material.

In another aspect, the invention provides a method for enhancing repair or regeneration of neural tissue at a site of injury in a mammalian subject comprising: introducing a composition comprising self-assembling peptides (SAPs), also referred to as sapeptides, into the subject at or in the vicinity of the site of injury, wherein the peptides are amphiphilic peptides that comprise substantially equal proportions of hydrophobic and hydrophilic amino acids and are complementary and structurally compatible. In certain embodiments of the invention the peptides self-assemble into a macroscopic structure, e.g., a beta-sheet macroscopic structure. "In the vicinity" of a site of injury refers to a location close enough to the site of injury that the composition can reach the site of injury in a therapeutically effective amount.

In another aspect, the invention provides a composition for enhancing regeneration or repair of neural tissue comprising: (i) a nanoscale structured material, or a precursor thereof, wherein the nanoscale structured material provides an environment that is permissive for regeneration of neural tissue and allows axon growth from one side of a site of injury or barrier to the other side of the site of injury or barrier; and (ii) a substance selected from the group consisting of: regeneration promoting factors, substances that counteract a molecule that inhibits regeneration or growth of neural tissue, nutrients, and templates for synthesis of a regeneration enhancing protein.

The invention further provides a composition for enhancing regeneration or repair of neural tissue comprising: (i) self-assembling peptides, wherein the peptides are amphiphilic peptides that comprise substantially equal proportions of hydrophobic and hydrophilic amino acids and are complementary and structurally compatible; and (ii) a substance selected from the group consisting of: regeneration promoting factors, substances that counteract a molecule that inhibits regeneration or growth of neural tissue, nutrients, and templates for synthesis of a regeneration enhancing protein. In certain embodiments of the invention the peptides self-assemble into a macroscopic structure, e.g., a beta-sheet macroscopic structure.

The invention further provides compositions and methods for replacement, repair, and/or regeneration of spinal tissue. In particular, the compositions and methods are of use for replacement, repair, and/or regeneration of intervertebral disc tissue, e.g., nucleus pulposus tissue. The intervertebral disc tissue to be replaced, repaired, or regenerated may be tissue that is damaged in an accident, during surgery, etc., or may be tissue that has degenerated or herniated for some other reason. The invention provides an intervertebral disc replacement. The invention further provides a nucleus pulposus replacement.

This application refers to various patents and publications. The contents of all of these are incorporated by reference. In addition, the following publications are incorporated herein by reference: *Current Protocols in Molecular Biology, Current Protocols in Immunology, Current Protocols in Protein Science*, and *Current Protocols in Cell Biology*, all John Wiley & Sons, N.Y., edition as of July 2002; Sambrook, Russell, and Sambrook, *Molecular Cloning: A Laboratory Manual*, 3$^{rd}$ ed., Cold Spring Harbor Laboratory Press, Cold Spring Harbor, 2001; Kandel, E., Schwartz, J. H., Jessell, T. M., (eds.), *Principles of Neural Science*, 4$^{th}$ ed., McGraw Hill, 2000. In addition, the references listed in [86] are incorporated herein by reference. In the event of a conflict between the instant specification and any of the incorporated references, the specification will control.

BRIEF DESCRIPTION OF THE DRAWING

FIG. 2 is a parasagittal view of an adult hamster brain showing a schematic representation of the lesion that transected the optic tract in the middle of the superior colliculus. Scale bar 500 microns.

FIG. 3 is a dorsal view reconstruction of the hamster brain with cortex removed. Rostral is to the right and caudal is to the left. The straight black line is the location of the transection of the optic tract made at postnatal day 2 (P2). Other areas of the brain shown include the superior colliculus (SC), pretectal area (PT), lateral posterior nucleus (LP), medial geniculate body (MGB), and inferior colliculus (IC).

FIG. 5A shows 24 hour survival cases. FIG. 5B shows 72 hour survival cases. In each panel, the image on the left shows lesions injected with SAP and Congo Red (similar to saline injected controls), while the image on the right shows lesions injected with SAP alone.

FIG. 6A shows images from two animals injected with SAP and Congo Red (similar to saline controls). FIG. 6B shows images from two animals injected with SAP alone.

DETAILED DESCRIPTION OF CERTAIN PREFERRED EMBODIMENTS OF THE INVENTION

I. Definitions

Figure 1:
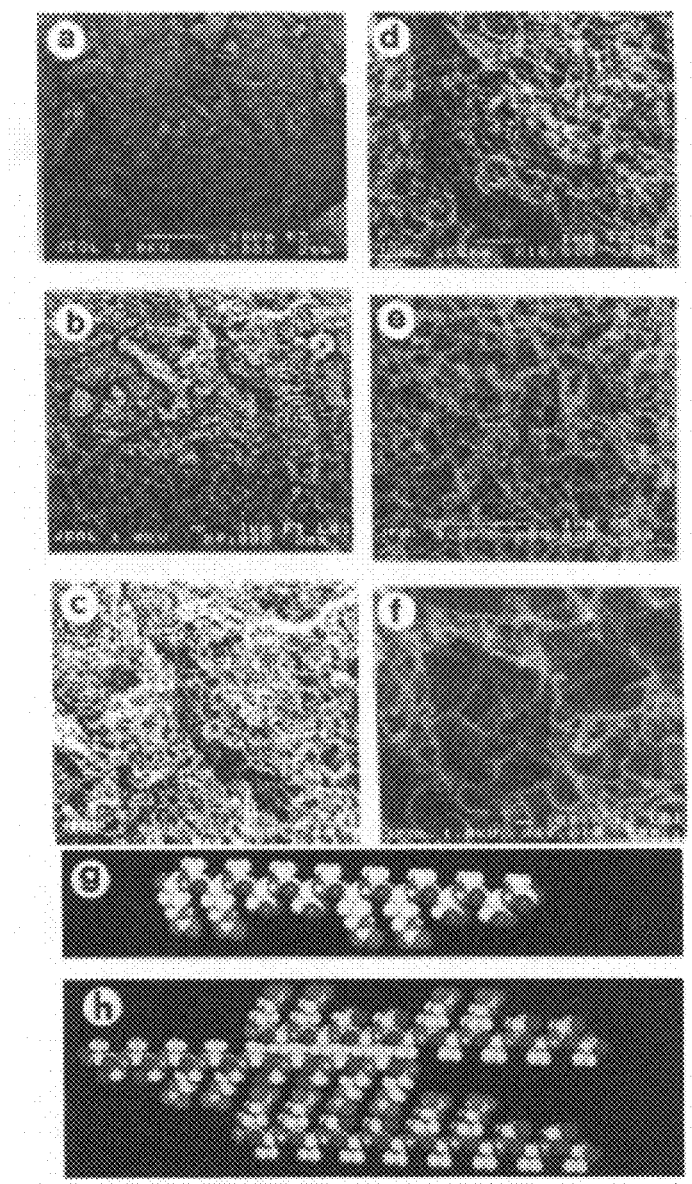
FIG. 1A-1F shows scanning electron microscope (SEM) images of a peptide hydrogel. At low magnifications the scaffold resembles felt (a-c). At high magnifications, the interwoven nanofibers in the structure can be seen (d-f).
FIGS. 1G and 1H show proposed molecular models of the self-assembly of peptides (in this case a peptide containing RADA (SEQ ID NO: 31) sequences). The alanines form an overlapping hydrophobic interaction on one side of the peptide. The arginines and aspartates form complementary ionic bonds on the other side. These ionic self-complementary can undergo molecular self-assembly.

The following definitions are of use in understanding the invention.

"Antibody" refers to an immunoglobulin, which may be natural or wholly or partially synthetically produced in various embodiments of the invention. An antibody may be derived from natural sources (e.g., purified from a rodent, rabbit, chicken (or egg) from an animal that has been immunized with an antigen or a construct that encodes the antigen) partly or wholly synthetically produced. An antibody may be a member of any immunoglobulin class, including any of the human classes: IgG, IgM, IgA, IgD, and IgE. The antibody may be a fragment of an antibody such as an Fab', $F(ab')_2$, scFv (single-chain variable) or other fragment that retains an antigen binding site, or a recombinantly produced scFv fragment, including recombinantly produced fragments. See, e.g., Allen, T., *Nature Reviews Cancer, Vol.* 2, 750-765, 2002, and references therein. Preferred antibodies, antibody fragments, and/or protein domains comprising an antigen binding site may be generated and/or selected in vitro, e.g., using techniques such as phage display (Winter, G. et al. 1994. *Annu. Rev. Immunol.* 12:433-455, 1994), ribosome display (Hanes, J., and Pluckthun, A. *Proc. Natl. Acad. Sci. USA.* 94:4937-4942, 1997), etc. In various embodiments of the invention the antibody is a "humanized" antibody in which for example, a variable domain of rodent origin is fused to a constant domain of human origin, thus retaining the specificity of the rodent antibody. It is noted that the domain of human origin need not originate directly from a human in the sense that it is first synthesized in a human being. Instead, "human" domains may be generated in rodents whose genome incorporates human immunoglobulin genes. See, e.g., Vaughan, et al., *Nature Biotechnology,* 16: 535-539, 1998. An antibody may be polyclonal or monoclonal, though for purposes of the present invention monoclonal antibodies are generally preferred.

"Approximately", as used herein, is generally taken to include numbers that fall within a range of 10% in either direction (greater than or less than) the number unless otherwise stated or otherwise evident from the context (except where such number would exceed 100% of a possible value). Where ranges are stated, the endpoints are included within the range unless otherwise stated or otherwise evident from the context.

"Biocompatible": A material is considered biocompatible with respect to cells if it is substantially non-toxic to cells in vitro, e.g., if its addition to cells in culture results in less than or equal to 20% cell death. A material is considered biocompatible with respect to a recipient, if it is substantially non-toxic to the recipient's cells in the quantities and at the location used, and also does not elicit or cause a significant deleterious or untoward effect on the recipient's body, e.g., an immunological or inflammatory reaction, unacceptable scar tissue formation, etc.

"Biodegradable" means capable of being broken down physically and/or chemically within cells or within the body of a subject, e.g., by hydrolysis under physiological conditions, by natural biological processes such as the action of enzymes present within cells or within the body, etc., to form smaller chemical species which can be metabolized and, optionally, reused, and/or excreted or otherwise disposed of. Preferably a biodegradable compound is biocompatible.

"Biomolecule", as used herein, a "biomolecule" refers to a molecule such as a protein, peptide, proteoglycan, lipid, carbohydrate, or nucleic acid having characteristics typical of molecules found in living organisms. A biomolecule may be naturally occurring or may be artificial (not found in nature and not identical to a molecule found in nature). For example, a protein having a sequence or modification resulting from the mental process of man, and not occurring in nature, is considered an artificial biomolecule. A protein (e.g., an oligonucleotide) having a sequence or modification resulting from the mental process of man, and not occurring in nature, is considered an artificial biomolecule.

"Chemotactic substance", as used herein, refers to a substance having the ability to recruit cells to a site at which the substance is present. Such cells may, for example, have the potential to contribute to the formation or repair of a tissue (e.g., by providing growth factors) or to contribute to an immune response. Certain chemotactic substances may also function as proliferation agents.

"Central nervous system": The central nervous system (CNS) includes the brain, spinal cord, optic, olfactory, and auditory systems. The CNS comprises both neurons and glial cells (neuroglia), which are support cells that aid the function of neurons. Oligodendrocytes, astrocytes, and microglia are glial cells within the CNS. Oligodendrocytes myelinate axons in the CNS, while astrocytes contribute to the blood-brain barrier, which separates the CNS from blood proteins and cells. Microglial cells serve immune system functions.

"Complementary" means having the capability of forming ionic or hydrogen bonding interactions between hydrophilic residues from adjacent peptides in the scaffold. Each hydrophilic residue in a peptide either hydrogen bonds or ionically pairs with a hydrophilic residue on an adjacent peptide, or is exposed to solvent. Pairing may also involve van der Waals forces.

"Effective amount", in reference to an active agent such as a self-assembling peptide or biomolecule, refers to the amount necessary to elicit a desired biological response. As will be appreciated by those of ordinary skill in this art, the effective amount of an agent may vary depending on such factors as the desired biological endpoint, the agent to be delivered, the nature of the site to which the agent is delivered, the nature of the conditions for which the agent is administered, etc. For example, the effective amount of a composition for treatment of an injury to the nervous system may be an amount sufficient to promote healing of an injury to a greater extent than would occur in the absence of the composition, and/or to promote axon regrowth to a greater extent than would occur in the absence of the composition. Axon regrowth can include axon extension, axon regrowth across a lesion or barrier, etc. An effective amount may be an amount sufficient to promote functional recovery of one or more nervous system functions to a greater extent than would occur in the absence of the composition.

"Gene therapy vector" refers to a vector, as defined below, that comprises a template for transcription of a therapeutic nucleic acid molecule (e.g., an siRNA strand, shRNA strand, antisense RNA strand, or ribozyme), or comprises a template for transcription of a nucleic acid molecule that is translated to produce a therapeutic polypeptide.

"Iso-osmotic solute" means a non-ionizing compound dissolved in an aqueous solution such that the resulting solution (an iso-osmotic solution) has an osmotic pressure or osmolality compatible with cell viability over periods of time greater than 1 minute, preferably greater than 5 minutes, yet more preferably greater than 10 minutes, yet more preferably at least 1 hour. In general, a preferred iso-osmotic solution has an osmotic pressure that approximates the osmotic pressure of the extracellular or intracellular environment of cells (e.g., in tissue culture medium, within a subject, etc.). For example, an iso-osmotic solution may have an osmotic pressure that is within 290±10 mosm/kg $H_2O$. Preferred iso-osmotic solutes include carbohydrates, such as monosaccharides or disaccharides. Examples of preferred carbohydrates include sucrose, glucose, galactose, fructose, ribose, mannose, arabinose, and xylose. Still another preferred iso-osmotic solute is glycerol, such as an aqueous solution of glycerol that is between 5 to 20% (v/v) glycerol.

"Macroscopic" means having dimensions large enough to be visible under magnification of 10-fold or less. In preferred embodiments of the invention a macroscopic structure is visible to the naked eye. A macroscopic structure may be transparent and may be two-dimensional, or three-dimensional. If two-dimensional, in certain embodiments of the invention it comprises more than a single layer of molecules, e.g., 2, 3, or more layers of molecules. Typically each dimension is at least 10 µm, in size. In certain embodiments at least two dimensions are at least 100 µm, or at least 1000 µm in size. Frequently at least two dimensions are at least 1-10 mm in size, 10-100 mm in size, or more. The relevant dimensions may be, e.g., length, width, depth, breadth, height, radius, diameter, circumference, in the case of structures that have a regular two or three-dimensional shape such as a sphere, cylinder, cube, etc., or an approximation of any of the foregoing in the case of structures that do not have a regular two or three-dimensional shape Other relevant dimensions may also be used.

"Microfiber", as used herein, refers to a fiber having a diameter of microscale dimensions. Typically a microscale fiber has a diameter of 500 µm or less, a diameter of less than 100 µm, a diameter of less than 50 µm, a diameter of less than 20 µm, a diameter of between 10 and 20 µm, or a diameter of between 5 and 10 µm.

"Microscale", as used herein, generally refers to structures having dimensions that may most conveniently be expressed in terms of micrometers. For example, the term "microscale structure" may refer to a structure having dimensions of approximately 500 µm or less, approximately 100 µm or less, approximately 50 µm or less, approximately 20-50 µm, approximately 10-20 µm, approximately 5-10 µm, approximately 1-5 µm, approximately 1 µm, or between 0.5 and 1 µm. One of ordinary skill in the art will recognize that the length of such structures may run into the millimeters, but that most dimensions are in the micrometer range.

"Nanofiber" refers to a fiber having a diameter of nanoscale dimensions. Typically a nanoscale fiber has a diameter of 500 nm or less. According to certain embodiments of the invention a nanofiber has a diameter of less than 100 nm. According to certain other embodiments of the invention a nanofiber has a diameter of less than 50 nm. According to certain other embodiments of the invention a nanofiber has a diameter of less than 20 nm. According to certain other embodiments of the invention a nanofiber has a diameter of between 10 and 20 nm. According to certain other embodiments of the invention a nanofiber has a diameter of between 5 and 10 nm. According to certain other embodiments of the invention a nanofiber has a diameter of less than 5 nm.

"Nanoscale", as used herein, generally refers to structures having dimensions that may most conveniently be expressed in terms of nanometers, or materials composed therefrom. For example, the term "nanoscale structured material" or "nanoscale scaffold" may refer to a material composed of structures (e.g., nanofibers) having dimensions of approximately 500 nm or less, approximately 100 nm or less, approximately 50 nm or less, approximately 20-50 nm, approximately 10-20 nm, approximately 5-10 nm, approximately 1-5 mm, approximately 1 nm, or between 0.1 and 1 nm. The ranges listed are assumed to include both endpoints. The relevant dimensions may be, e.g., length, width, depth, breadth, height, radius, diameter (e.g., pore diameter), circumference, in the case of structures that do not have a regular two or three-dimensional shape such as a sphere, cylinder, cube, etc., or an approximation of any of the foregoing, e.g., in the case of structures that do not have a regular two or three dimensional shape. Any other relevant dimensions may also be used to determine whether a material is a nanoscale structured material, depending, for example on the shape of a structure formed therefrom. One of ordinary skill in the art will recognize that one or more dimensions of a nanoscale structure need not be in the nanometer range. For example, the length of such structures may run into the micron range or longer. However, generally most dimensions are in the nanometer range.

"Nanoscale environment scaffold" or "nanoscale environment structure" refers to a scaffold or structure comprising nanofibers. According to certain embodiments of the invention at least 50% of the fibers comprising the scaffold or structure are nanofibers. According to certain embodiments of the invention at least 75% of the fibers comprising the scaffold or structure are nanofibers. According to certain embodiments of the invention at least 90% of the fibers comprising the scaffold or structure are nanofibers. According to certain embodiments of the invention at least 95% of the fibers comprising the scaffold or structure are nanofibers. According to certain embodiments of the invention at least 99% of the fibers comprising the scaffold or structure are nanofibers. Of course the scaffold or structure may also comprise non-fiber constituents, e.g., water, ions, growth and/or differentiation-inducing agents such as growth factors, therapeutic agents, or other compounds, which may be in solution in the scaffold or structure and/or bound to the scaffold or structure. The term "scaffold" is not intended to impose any functional or structural limitation on a composition of the invention but merely serves to indicate that the composition may, for example, provide a supporting framework for axon extension or growth, cell or tissue growth, cell migration, extracellular matrix deposition, etc.

"Neural tissue", for purposes of this invention, refers to one or more components of the central nervous system and/or peripheral nervous system. Such components include brain tissue and nerves. In general, brain tissue and nerves contain neurons (which typically comprise cell body, axon, and dendrite(s)), glial cells (e.g., astrocytes, oligodendrocytes, and microglia in the CNS; Schwann cells in the PNS). It will be appreciated that brain tissue and nerves typically also contain various noncellular supporting materials such as extracellular matrix components, basal lamina (in the PNS), endoneurium, perineurium, and epineurium in nerves, etc. Additional normeural cells such as fibroblasts, endothelial cells, macrophages, etc., are typically also present. See [86] for further description of the structure of various neural tissues.

"Operably linked or operably associated" refers to a relationship between two nucleic acid sequences wherein the expression of one of the nucleic acid sequences is controlled by, regulated by, modulated by, etc., the other nucleic acid sequences, or a relationship between two polypeptides wherein the expression of one of the polypeptides is controlled by, regulated by, modulated by, etc., the other polypeptide. For example, the transcription of a nucleic acid sequence is directed by an operably linked promoter sequence; post-transcriptional processing of a nucleic acid is directed by an operably linked processing sequence; the translation of a nucleic acid sequence is directed by an operably linked translational regulatory sequence; the transport, stability, or localization of a nucleic acid or polypeptide is directed by an operably linked transport or localization sequence; and the post-translational processing of a polypeptide is directed by an operably linked processing sequence. Preferably a nucleic acid sequence that is operably linked to a second nucleic acid sequence, or a polypeptide that is operatively linked to a second polypeptide, is covalently linked, either directly or indirectly, to such a sequence, although any effective three-dimensional association is acceptable.

"Peptide", "polypeptide", or "protein", as used herein, refers to a string of at least two amino acids linked together by peptide bonds. A peptide generally represents a string of between approximately 2 and 200 amino acids, more typically between approximately 6 and 64 amino acids. Typically, the self-assembling portion of a self-assembling peptide is about 8-24, frequently about 12-20, or 16-20 amino acids. Peptide may refer to an individual peptide or a collection of peptides. Inventive peptides typically contain only natural amino acids, although non-natural amino acids (i.e., compounds that do not occur in nature but that can be incorporated into a polypeptide chain; see, for example, the Web site having URL www.cco.caltech.edu/~dadgrp/Unnatstruct.gif, which displays structures of non-natural amino acids that have been successfully incorporated into functional ion channels) and/or amino acid analogs as are known in the art may alternatively be employed. In particular, D amino acids may be used. Also, in various embodiments of the invention one or more of the amino acids in an inventive peptide may be altered or derivatized, for example, by the addition of a chemical entity such as an acyl group, a carbohydrate group, a carbohydrate chain, a phosphate group, a farnesyl group, an isofarnesyl group, a fatty acid group, a linker for conjugation or functionalization, etc. In certain embodiments of the invention a peptide is branched, in which case it contains at least two amino acid polymers, each of which consists of at least 3 amino acids joined by peptide bonds, but the two amino acid polymers themselves are not linked by a peptide bond.

"Peripheral nervous system (PNS)", for purposes of the present invention, includes the cranial nerves arising from the brain (other than the optic and olfactory nerves), the spinal nerves arising from the spinal cord, sensory nerve cell bodies, and their processes, i.e., all nervous tissue outside of the CNS. The PNS comprises both neurons and glial cells (neuroglia), which are support cells that aid the function of neurons. Glial cells within the PNS are known as Schwann cells, and serve to myelinate axons by providing a sheath that surrounds the axons. In various embodiments of the invention the methods and compositions described herein are applied to different portions of the PNS.

"Polynucleotide" or "oligonucleotide" refers to a polymer of nucleotides. As used herein, an oligonucleotide is typically less than 100 nucleotides in length. A polynucleotides or oligonucleotide may also be referred to as a nucleic acid. Naturally occurring nucleic acids include DNA and RNA. Typically, a polynucleotide comprises at least three nucleotides. A nucleotide comprises a nitrogenous base, a sugar molecule, and a phosphate group. A nucleoside comprises a nitrogenous base linked to a sugar molecule. In a polynucleotide or oligonucleotide, phosphate groups covalently link adjacent nucleosides to form a polymer. The polymer may include natural nucleosides (e.g., adenosine, thymidine, guanosine, cytidine, uridine, deoxyadenosine, deoxythymidine, deoxyguanosine, and deoxycytidine), nucleoside analogs (e.g., 2-aminoadenosine, 2-thiothymidine, inosine, pyrrolo-pyrimidine, 3-methyl adenosine, C5-propynylcytidine, C5-propynyluridine, C5-bromouridine, C5-fluorouridine, C5-iodouridine, C5-methylcytidine, 7-deazaadenosine, 7-deazaguanosine, 8-oxoadenosine, 8-oxoguanosine, O(6)-methylguanine, and 2-thiocytidine), chemically modified bases, biologically modified bases (e.g., methylated bases), intercalated bases, modified sugars (e.g., 2'-fluororibose, ribose, 2'-deoxyribose, arabinose, and hexose). The phosphate groups in a polynucleotide or oligonucleotide are typically considered to form the internucleoside backbone of the polymer. In naturally occurring nucleic acids (DNA or RNA), the backbone linkage is via a 3' to 5' phosphodiester bond. However, polynucleotides and oligonucleotides containing modified backbones or non-naturally occurring internucleoside linkages can also be used in the present invention. Such modified backbones include ones that have a phosphorus atom in the backbone and others that do not have a phosphorus atom in the backbone. Examples of modified linkages include, but are not limited to, phosphorothioate and 5'-N-phosphoramidite linkages. See U.S. Patent Application No. 20040092470 and references therein for further discussion of various nucleotides, nucleosides, and backbone structures that can be used in the polynucleotides or oligonucleotides described herein, and methods for producing them. Polynucleotides and oligonucleotides need not be uniformly modified along the entire length of the molecule. For example, different nucleotide modifications, different backbone structures, etc., may exist at various positions in the polynucleotide or oligonucleotide. Any of the polynucleotides described herein, including siRNAs, shRNAs, ribozymes, antisense RNAs, may utilize these modifications.

The polynucleotides may be of any size or sequence, and they may be single- or double-stranded. A polynucleotide may be, for example, a modified or unmodified circular plasmid, a linearized plasmid, a cosmid, a viral genome, a modified viral genome, an artificial chromosome, etc. In certain preferred embodiments, the polynucleotide is greater than 100 base pairs long. In certain other preferred embodiments, the polynucleotide is greater than 1000 base pairs long and may be greater than 10,000 base pairs long. The polynucleotide is preferably purified and substantially pure. Preferably, the polynucleotide is greater than 50% pure, more preferably greater than 75% pure, and most preferably greater than 95% pure. The polynucleotide may be provided by any means known in the art. In certain preferred embodiments, the polynucleotide has been engineered using recombinant techniques (for a more detailed description of these techniques, please see Ausubel et al. Current Protocols in Molecular Biology (John Wiley & Sons, Inc., New York, 1999); Molecular Cloning: A Laboratory Manual, 2nd Ed., ed. by Sambrook, Fritsch, and Maniatis (Cold Spring Harbor Laboratory Press: 1989). The polynucleotide may also be obtained from natural sources and purified from contaminating components found normally in nature. The polynucleotide may be synthesized using enzymatic techniques, either within cells or in vitro. The polynucleotide may also be chemically synthesized in a laboratory. In a preferred embodiment, the polynucleotide is synthesized using standard solid phase chemistry. The polynucleotide may be modified by chemical or biological means. In certain preferred embodiments, these modifications lead to increased stability of the polynucleotide. Modifications include methylation, phosphorylation, end-capping, etc.

"Proliferation agent" and "mitogenic agent" are used herein interchangeably to refer to the ability of a substance to enhance the proliferation of cells.

"Regeneration", as used in reference to regeneration of neural tissue in various embodiments of the invention, may include any aspect of anatomical or functional restoration of the condition of the neural tissue prior to an injury, which involves production of new neural tissue (by which is meant either cells or portions of cells). In certain embodiments of the invention production of new neural tissue includes growth (e.g., increase in size along one or more dimension, increase in volume, etc.) of existing cells, e.g., neurons. Regeneration may thus include growth of axons or other neuron processes. Such processes may arise directly from the cell body or may be extensions of processes that were severed or damaged due to injury. The new tissue may replace tissue that was previously present. In certain embodiments of the invention production of new neural tissue includes division of existing cells (cell proliferation).

"Repair", as used in reference to the repair of neural tissue in various embodiments of the invention, may include any aspect of anatomical or functional restoration of the condition of the neural tissue prior to an injury. For example, it may include restoration of physical continuity between portions of tissue that were separated by an injury. Preferably such restoration of physical continuity includes reapposition or reconnection of the portions of tissue without appreciable separation by tissue of a type that was not present prior to the injury, such as scar tissue. Repair may thus include filling of a defect in neural tissue, preferably by reapposition of portions of tissue separated by the defect and/or by growth of new neural tissue, rather than by development of scar tissue. Repair may, but need not, include growth or development of new tissue. Thus regeneration may be considered one aspect of repair, but repair can occur without evidence of new tissue growth.

"Small molecule" refers to organic compounds, whether naturally-occurring or artificially created (e.g., via chemical synthesis) that have relatively low molecular weight and that are not proteins, polypeptides, or nucleic acids. Typically, small molecules have a molecular weight of less than about 1500 g/mol. Also, small molecules typically have multiple carbon-carbon bonds.

"Solution that is substantially free of ions" means a solution to which no ions (or salts thereof) have been added or in which the concentration of ions (or salts thereof) is less than 0.01 or 0.001 mM.

"Structurally compatible" means capable of maintaining a sufficiently constant intrapeptide distance to allow structure formation. In certain embodiments of the invention the variation in the intrapeptide distance is less than 4, 3, 2, or 1 angstroms. It is also contemplated that larger variations in the intrapeptide distance may not prevent structure formation if sufficient stabilizing forces are present. This distance may be calculated based on molecular modeling or based on a simplified procedure that has been previously reported (U.S. Pat. No. 5,670,483). In this method, the intrapeptide distance is calculated by taking the sum of the number of unbranched atoms on the side-chains of each amino acid in a pair. For example, the intrapeptide distance for a lysine-glutamic acid ionic pair is 5+4=9 atoms, and the distance for a glutamine-glutamine hydrogen bonding pair is 4+4=8 atoms. Using a conversion factor of 3 angstroms per atom, the variation in the intrapeptide distance of peptides having lysine-glutamic acid pairs and glutamine-glutamine pairs (e.g., 9 versus 8 atoms) is 3 angstroms.

"Subject", as used herein, refers to an individual to whom an agent is to be delivered, e.g., for experimental, diagnostic, and/or therapeutic purposes. Preferred subjects are mammals, particularly domesticated mammals (e.g., dogs, cats, etc.), primates, or humans.

"Therapeutic molecule, substance, compound, or agent" refers to a molecule or combination of molecules of any type that, when administered to a subject in need thereof, alleviates one or more symptoms of a disease or undesired clinical condition, reduces the severity of a disease or clinical condition, prevents or lessens the likelihood of development of a disease or undesired clinical condition, or facilitates repair or regeneration of tissue in a manner other than simply providing general nutritional support to the subject. It is to be understood that a therapeutic molecule is generally to be administered in an effective amount, i.e., an amount sufficient to achieve a clinically significant result. A therapeutic molecule can be a small molecule, a biomolecule, etc. See *Goodman and Gilman's The Pharmacological Basis of Therapeutics*, $10^{th}$ Ed., and Katzung, *Basic and Clinical Pharmacology*, for examples.

"Treating", as used herein, can generally include reversing, alleviating, inhibiting the progression of, preventing or reducing the likelihood of the disease, disorder, or condition to which such term applies, or one or more symptoms or manifestations of such disease, disorder or condition. "Preventing" refers to causing a disease, disorder, condition, or symptom or manifestation of such, or worsening of the severity of such, not to occur.

"Vector" is used herein to refer to a nucleic acid or a virus or portion thereof (e.g., a viral capsid) capable of mediating entry of, e.g., transferring, transporting, etc., a nucleic acid molecule into a cell. Where the vector is a nucleic acid, the nucleic acid molecule to be transferred is generally linked to, e.g., inserted into, the vector nucleic acid molecule. A nucleic acid vector may include sequences that direct autonomous replication (e.g., an origin of replication), or may include sequences sufficient to allow integration of part of all of the nucleic acid into host cell DNA. Useful nucleic acid vectors include, for example, DNA or RNA plasmids, cosmids, and naturally occurring or modified viral genomes or portions thereof or nucleic acids (DNA or RNA) that can be packaged into viral capsids. Plasmid vectors typically include an origin of replication and one or more selectable markers. Plasmids may include part or all of a viral genome (e.g., a viral promoter, enhancer, processing or packaging signals, etc.). Viruses or portions thereof (e.g., viral capsids) that can be used to introduce nucleic acid molecules into cells are referred to as viral vectors. Useful viral vectors include adenoviruses, retroviruses, lentiviruses, vaccinia virus and other poxviruses, herpex simplex virus, and others. Viral vectors may or may not contain sufficient viral genetic information for production of infectious virus when introduced into host cells, i.e., viral vectors may be replication-defective, and such replication-defective viral vectors may be preferable for therapeutic use. Where sufficient information is lacking it may, but need not be, supplied by a host cell or by another vector introduced into the cell. The nucleic acid to be transferred may be incorporated into a naturally occurring or modified viral genome or a portion thereof or may be present within the virus or viral capsid as a separate nucleic acid molecule. It will be appreciated that certain plasmid vectors that include part or all of a viral genome, typically including viral genetic information sufficient to direct transcription of a nucleic acid that can be packaged into a viral capsid and/or sufficient to give rise to a nucleic acid that can be integrated into the host cell genome and/or to give rise to infectious virus, are also sometimes referred to in the art as viral vectors. Where sufficient information is lacking it may, but need not be, supplied by a host cell or by another vector introduced into the cell.

II. Overview

The development of new biological materials, particularly biologically compatible materials that serve as permissive substrates for cell growth, differentiation, and biological function has broad implications for advancing medical technology and for understanding basic biological characteristics of cells. The present invention relates to materials and techniques for enhancing repair and/or regeneration of neural tissue using biocompatible materials that can serve as scaffolds or components to support regrowth of neural tissue after injury. The materials can also serve as delivery agents for biologically active molecules that enhance the processes of regeneration and/or repair. The materials create an environment that is permissive for regeneration and repair of neural tissue, i.e., in the presence of the materials neural tissue exhibits an enhanced capacity for regeneration and/or repair. It is noted that materials that create an environment permissive for regeneration may be used for the creation of neural tissue structures that were not initially present in the subject, rather than merely for restoration of previously existing structures. For example, creation of an environment permissive for regeneration will allow the creation of neural tissue bridges around or through barriers such as areas of necrosis or scar tissue. It will also allow the creation of new connections between different portions of the brain (or elsewhere in the nervous system), i.e., connections that do not necessarily resemble structures that exist normally.

The inventors have previously described a class of biomaterials that are made through self-assembly of ionic or polar self-complementary peptides (See, e.g., references 32-24, 36, 38, 39 and U.S. Pat. Nos. 5,955,343 and 5,670,483). These peptides are able to form hydrogels when contacted with water. In certain embodiments of the invention these hydrogels contain approximately 99% or greater water content. The peptides self-assemble into membranes or three-dimensional structures upon exposure to a sufficient concentration of ions in solution, to form a stable macroscopic porous matrix composed of orderly interwoven filaments approximately 10-20 nm in diameter, with pore size on the order of 50-100 nm in linear dimension. An important characteristic of these materials is that their properties and mechanical strength can be controlled through manipulation of peptide parameters [33, 37-39]. For example, it has been shown that the stiffness of the gel increases strongly with peptide concentration [39]. The sequences, characteristics, and properties of the peptides and the structures formed by them upon self-assembly are further discussed in the next section.

The inventors have shown that these peptide structures are able to support cell attachment, viability, and growth when cells are cultured on the surface of the structure. In addition, the structures are able to serve as substrates for neurite outgrowth and synapse formation when neurons are grown on their surface [32]. In addition, the inventors have shown that it is possible to encapsulate cells within the peptide hydrogels, thus placing the cells in a three-dimensional arrangement within the peptide scaffold, and that the cells maintain viability and function when so encapsulated (see pending U.S. patent application Ser. No. 09/778,200, filed Feb. 6, 2001, Entitled "Peptide Scaffold Encapsulation Of Tissue Cells And Uses Thereof" and Ser. No. 10/196,942 entitled "Liver Cellular Reprogramming in Peptide Hydrogel and Uses Thereof").

The results described above indicated that the peptide structures could support the growth of cell lines and of cells isolated from the body in vitro. The work indicated that the peptides provide a favorable environment for neuron attachment and synapse formation in culture and also showed that they do not elicit a detectable immune system response when implanted into a mammalian subject. However, this work did not address the possibility of employing the peptides to enhance repair or regeneration of injured nervous tissue in vivo, i.e., in intact mammalian subjects. In particular, the previous work did not address the possibility of employing the peptides to enhance repair or regeneration of injured neural tissue in the CNS, where significant obstacles to such repair exist.

The nervous system possesses a number of distinctive characteristics, indicating that strategies useful for repair of other body tissues will not necessarily be effective for repair of nervous system tissues, and vice versa. For example, nerves must regenerate with the correct directionality to innervate the appropriate target cells. Thus features common to wound healing, such as development of scar tissue, often create barriers that prevent functional repair. In addition, the presence of fluid-filled cavities within the nervous system, which often arise after injury, may prevent regenerating axons from reaching the target location.

The response of neurons to injury is unique in a number of respects. First of all, unlike many cells in the body, neurons are unable to undergo mitosis. Their ability to regenerate a severed portion or to sprout new processes (e.g., axons), varies depending on the particular neural tissue involved. In the PNS, following a complete nerve transection the distal portion of the nerve begins to degenerate as a consequence of separation from the cell body and activity of proteases. The proximal portion of the nerve swells, but there is relatively little retrograde degradation. Phagocytic cells such as macrophages and Schwann cells clear myelin and other debris from the degenerating axons in addition to producing molecules such as cytokines and neurotrophic factors shown to enhance axon growth. Regeneration then begins from the proximal portion as new axons sprout and extend. In humans, this typically occurs at a rate of approximately 2-5 mm/day. Functional recovery requires that the axons be able to find their distal target. Thus large gaps and barriers within the tissue can compromise the extent to which full recovery of function is achieved.

The CNS represents a unique environment in a number of respects. First, the blood-brain or blood-spine barrier isolates the CNS from the rest of the body. This may alter the wound healing process, since it alters access by cells such as macrophages that typically migrate to a site of injury, where they play a number of roles, including removal of debris. Furthermore, the CNS is bathed in cerebrospinal fluid (CSF), which has a unique chemical composition and may react differently with implanted materials than the extracellular fluids found elsewhere in the body.

In contrast to neurons in the PNS, CNS axons do not typically undergo significant regeneration under native conditions for a number of reasons. The physiological response to injury in the CNS differs to that in the PNS in that, for example, infiltration of the injury site by phagocytic cells such as macrophages is slower, resulting in slower clearance of debris such as myelin, which can inhibit axon growth. As discussed further below, a number of molecules that inhibit axon growth are found at sites of injury in the CNS, and astrocyte proliferation typically results in formation of scar tissue, which can inhibit regeneration. In addition, there appears to be little upregulation of expression of endogenous growth-promoting molecules in the CNS. In short, the CNS following injury does not present an environment permissive for regeneration and repair of neural tissue.

The present invention encompasses the discovery that introducing a biocompatible material having a nanoscale structure at a site of injury within the nervous system results in creation of an environment that is permissive for such regeneration and repair. Unlike the great majority of natural or artificial materials that have been used heretofore in an effort to facilitate nerve regeneration, the materials of the present invention interact with cells on a nanoscale rather than a microscale. The materials are made of nanofibers rather than the microfibers typical of various other materials whose use for this purpose has been proposed. While not wishing to be bound by any theory, it is believed that the small size of the fibers and/or the open weave structure of the materials promote extension of cell processes and allow diffusion of nutrients, waste products, etc., in a manner that provides unique advantages for neural tissue regeneration. In certain embodiments of the invention the nanofibers that comprise the material are ordered during self assembly in a complementary fashion due to weak interactive molecular forces. In certain embodiments of the invention the nanofibers that comprise the material are randomly ordered. In other words, while the fibers may have an orderly internal structure, they may lack directionality or alignment with respect to one another. For example, the fibers may not be substantially parallel to one another. In addition, in certain embodiments of the invention the fibers lack directionality with respect to the injury or to locations proximal or distal to the site of injury.

In general, the invention provides a method for enhancing repair or regeneration of neural tissue at a site of injury in a mammalian subject comprising: providing a nanoscale structured material at or in the vicinity of the site of injury, wherein the nanoscale structured material provides an environment that is permissive for regeneration of neural tissue and allows axon growth from one side of a site of injury or barrier to the other side of site of injury or barrier. In other words, the injury or barrier (which can be, for example, a tissue barrier such as necrotic tissue, scar tissue, or a fluid-filled cavity) initially separates a first location in which a regenerating axon is located, from a second location. The nanoscale structured material can be provided by introducing a precursor of the material, e.g., a composition comprising components that assemble to form the material, at or in the vicinity of a site of injury. An axon or portion thereof is present at the first location. Presence of the material allows the axon to extend such that a portion of the axon is present at the second location. The first location can be on either side of the injury or barrier. The two sides of the injury or barrier may be identified by reference to the location of a cell body from which a regenerating axon extends. For example, the side of the injury or barrier on which the cell body of a regenerating axon is located may be referred to as being proximal to the site of injury. The side of the injury or barrier on which the cell body is not located may be referred to as being distal to the site of injury. The presence of the nanoscale structured material provides an environment that allows axon growth from a location proximal to a site of injury or barrier to a location distal to the site of injury or barrier. Thus the invention provides a method for enhancing repair or regeneration of neural tissue at a site of injury in a mammalian subject comprising: providing a nanoscale structured material at the site of injury, wherein the nanoscale structured material provides an environment that is permissive for regeneration of neural tissue and allows axon growth from a location proximal to a site of injury or barrier to a location distal to the site of injury or barrier. It will be appreciated that in the case of certain injuries or barriers, particularly in the CNS, cell bodies will be present on both sides of the injury or barrier, in which case there can be bilateral growth. For example, if an injury or barrier exists between two locations in the brain, axons emerging from cell bodies at each location can regenerate towards the other side of the lesion. The injury or barrier may, for example, transect axons that extend between different regions of the brain, between two nuclei (discrete collections of neurons), etc.

The regeneration process involves extension of the axon and also may involve a "knitting together" of the two sides of the injury, so that an initial gap comes to be filled with living tissue. It is to be understood that the phrase "at a site of injury" includes locations in close proximity to such a site, such that the material may readily come into physical contact with tissue on one or both sides of the injury. The injury can be any event that causes nerve damage, such that axons are separated from their targets. For example, the injury may be due to surgery, external trauma, stroke, or conditions such as tumors. The injury may be caused by prior administration of an agent such as an aminoglycoside antibiotic or neurotoxin, which causes damage to neural tissue.

The target can either be the natural target of such axon, i.e., the cell or cells on which such axon formed synapse(s) prior to injury, or a new target. In the latter case, the invention encompasses the introduction of nanoscale structured materials at a site of injury to direct regenerating axons to innervate targets with which they were not initially in communication prior to the injury. For example, the methods and compositions of the invention may be used in reconstructive brain surgery, in which axons are routed so as to form new functional connections that replace or compensate for neural tissue that has been permanently lost.

According to certain embodiments of the invention the nanoscale structured material is provided by introducing a precursor of the material into or in the vicinity of a site of injury. By "precursor" is meant a composition comprising component(s) that can assemble to form the nanoscale structured material. In certain embodiments of the invention the components can assemble in situ (i.e., within the body of a subject) The nanoscale structured material may include, and/or its assembly may involve, additional components present in situ, e.g., ions. In certain embodiments the nanoscale structured material is provided by introducing a composition comprising self-assembling peptides into a subject at or in the vicinity of a site of injury to the nervous system. The peptides may be provided, for example, in solution or in the form of a gel (i.e., already assembled). In general, the amount of material introduced at or in the vicinity of the site of injury will vary depending on various factors such as the size or extent of the injury. For example, the volume introduced may range from a few microliters to several milliliters or more, e.g., tens of milliliters. The following section provides details regarding certain self-assembling peptides suitable for use in the present invention, mechanisms by which self-assembly occurs, and methods by which the process of self-assembly and/or the features of the assembled structure may be controlled. Subsequent sections describe the methods and compositions of the invention in further detail.

III. Self-Assembling Peptides

In certain preferred embodiments of the invention the nanoscale structured material comprises self-assembling peptides. These peptides comprise a family of complementary and structurally compatible molecules. The peptides and their properties are described in U.S. Pat. Nos. 5,955,343 and 5,670,483 and in co-pending U.S. patent application Ser. Nos. 09/778,200, and 10/196,942. Prior to self-assembly the peptides may be dissolved in a solution that is substantially free of monovalent ions or contains only a low concentration of such ions, e.g., less than 10, 5, 1, or 0.1 mM. Self-assembly may be initiated by the addition of an ionic solute to a peptide solution or by a change in pH [37, 38]. For example, NaCl at a concentration of between 5 mM and 5 M induces the assembly of macroscopic structures within a few minutes. Lower concentrations of NaCl may also induce assembly but at a slower rate. Alternately, self-assembly may be initiated by introducing the peptides (preferably dissolved in a solution that is substantially free of monovalent ions) into a solution comprising such ions, e.g., a physiological fluid such as CSF. The peptides can thus self-assemble at a location in vivo. Preferred ions include monovalent cations such as $Li^+$, $Na^+$, $K^+$, and $Cs^+$. Preferably, the concentration of the ion is at least 5, 10, 20, or 50 mM in order to induce self-assembly. One of ordinary skill in the art will be able to select preferred concentrations of ions based on the particular peptide and desired speed of assembly.

In certain embodiments of the invention peptides forming the macroscopic structure contain between 8 and 200 amino acids, 8 to 36 amino acids, or 8 to 16 amino acids, inclusive. In certain embodiments of the invention the concentration of the peptides prior to self-assembly is between 0.01% (0.1 mg/ml) and 99.99% (999.9 mg/ml), inclusive. In certain embodiments of the invention the concentration of the peptides prior to self-assembly is between 0.1% (1 mg/ml) and 10% (100 mg/ml), inclusive. In certain embodiments of the invention the concentration of the peptides prior to self-assembly is between 0.1% (1 mg/ml) and 5% (50 mg/ml), inclusive, or between 0.5% (5 mg/ml) and 5% (50 mg/ml), inclusive. In certain embodiments of the invention the concentration of the peptides prior to self-assembly is approximately 5 mg/ml, approximately 10 mg/ml, approximately 15 mg/ml, or approximately 20 mg/ml. In certain embodiments of the invention the peptides are administered dry, e.g., in powder form, to a site of injury. The peptides may then self-assemble following contact with body fluids at the site of injury, e.g., at a fluid-filled cavity in the CNS.

If desired, peptide scaffolds may be formed with a predetermined shape or volume. To form a scaffold with a desired geometry or dimension, an aqueous peptide solution may be placed in a pre-shaped casting mold, and the peptides induced to self-assemble into a scaffold by the addition of an ion, as described herein. Alternately, the ion may be added to the peptide solution shortly before placing the solution into the mold, provided that care is taken to place the solution into the mold before substantial assembly occurs. The resulting material characteristics, time required for assembly, and geometry and dimensions of the macroscopic peptide scaffold are governed by the concentration and amount of peptide solution that is applied, the concentration of ion used to induce assembly of the scaffold, and the dimensions of the casting apparatus. Cells and agents such as bioactive molecules (e.g., therapeutic compounds), may be introduced into the peptide solution prior to self-assembly. The self-assembly process then forms a structure that encapsulates the cells or molecules. To achieve even distribution of the cells or molecules within the structure it may be desirable to thoroughly mix the solution prior to initiation of self-assembly. It may be desirable to maintain the cells or agents in a solution that contains substantially no ions or only low concentration of ions in order to avoid initiation of self-assembly immediately upon combining the cells or agents with the peptide solution. In this case the cells are preferably maintained in an iso-osmotic solute such as sucrose prior to combination with the peptide solution.

The side-chains of the peptides partition into two faces, a polar face with charged ionic side chains and a nonpolar face with alanines or other hydrophobic groups. These ionic side chains are self-complementary to one another in that the positively charged and negatively charged amino acid residues can form complementary ionic pairs. These peptides are therefore called ionic, self-complementary peptides, or Type I self-assembling peptides. If the ionic residues alternate with one positively and one negatively charged residue (-+-+-+-+), the peptides are described as "modulus I;" if the ionic residues alternate with two positively and two negatively charged residues (--++--++), the peptides are described as "modulus II."

Many modulus I and II self-complementary peptides such as EAKA16-I, RADA16-I, RAEA16-I, and KADA16-I have been analyzed previously (Table 1). These peptides are also referred to as RAD16-I, RAE16-I, KAD16-I, etc. Modulus IV ionic self-complementary peptides containing 16 amino acids; such as EAK16-IV, KAE16-IV, DAR16-IV and RAD16-IV; have also been studied. If the charged residues in these self-assembling peptides are substituted (i.e., the positive charged lysines are replaced by positively charged arginines and the negatively charged glutamates are replaced by negatively charged aspartates), there are essentially no significant effects on the self-assembly process. However, if the positively charged residues, lysine and arginine are replaced by negatively charged residues, aspartate and glutamate, the peptides can no longer undergo self-assembly to form macroscopic structures; however, they can still form a beta-sheet structure in the presence of salt. Other hydrophilic residues, such as asparagine and glutamine, that form hydrogen bonds may be incorporated into the peptides instead of or in addition to charged residues. If the alanines in the peptides are changed to more hydrophobic residues, such as leucine, isoleucine, phenylalanine or tyrosine, these peptides have a greater tendency to self-assemble and form peptide matrices with enhanced strength. Some peptides that have similar compositions and lengths as these aforementioned peptides form alpha-helices and random-coils rather than beta-sheets and do not form macroscopic structures. Thus, in addition to self-complementarity, other factors are likely to be important for the formation of macroscopic structures, such as the peptide length, the degree of intermolecular interaction, and the ability to form staggered arrays.

It is noted that in certain embodiments of the invention a group or radical such as an acyl group (RCO—, where R is an organic group), e.g., an acetyl group ($CH_3CO$—) is present at the N terminus of the peptides in order to neutralize an extra charge positive that may otherwise be present (e.g., a charge not resulting from the side chain of the N-terminal amino acid). Similarly, a group such as an amine group ($NH_2$) may be used to neutralize an extra negative charge that may otherwise be present at the C terminus (e.g., a charge not resulting from the side chain of C-terminal amino acid), thus converting the C terminus into an amide (—$CONH_2$). While not wishing to be bound by any theory, the neutralization of charges on the terminal N and C molecules may facilitate self-assembly. One of ordinary skill in the art will be able to select other suitable groups.

Self-assembled nanoscale scaffolds can be formed with varying degrees of stiffness or elasticity. The peptide scaffolds typically have a low elastic modulus, in the range of 1-10 kPa as measured in a standard cone-plate rheometer. Such low values permit scaffold deformation as a result of cell contraction, and this deformation may provide the means for cell-cell communication. Scaffold stiffness can be controlled by a variety of means including changes in peptide sequence, changes in peptide concentration, and changes in peptide length [37, 38]. Other methods for increasing stiffness can also be used, such as by attaching a biotin molecule to the amino- or carboxy-terminus of the peptides or between the amino- and carboxy-termini, which may then be cross-linked.

TABLE 1

Representative Self-Assembling Peptides

| Name | Sequence (n-->c) | Modulus | |
|---|---|---|---|
| RADA16-I | n-RADARADARADARADA-c | I | (SEQ ID NO: 1) |
| RGDA16-I | n-RADARGDARADARGDA-c | I | (SEQ ID NO: 2) |
| RADA8-I | n-RADARADA-c | I | (SEQ ID NO: 3) |
| RAD16-II | n-RARADADARARADADA-c | II | (SEQ ID NO: 4) |
| RAD8-II | n-RARADADA-c | II | (SEQ ID NO: 5) |
| EAKA16-I | n-AEAKAEAKAEAKAEAK-c | I | (SEQ ID NO: 6) |
| EAKA8-I | n-AEAKAEAK-c | I | (SEQ ID NO: 7) |
| RAEA16-I | n-RAEARAEARAEARAEA-c | I | (SEQ ID NO: 8) |
| RAEA8-I | n-RAEARAEA-c | I | (SEQ ID NO: 9) |
| KADA16-I | n-KADAKADAKADAKADA-c | I | (SEQ ID NO: 10) |
| KADA8-I | n-KADAKADA-c | I | (SEQ ID NO: 11) |
| EAH16-II | n-AEAEAHAHAEAEAHAH-c | II | (SEQ ID NO: 12) |
| EAH8-II | n-AEAEAHAH-c | II | (SEQ ID NO: 13) |
| EFK16-II | n-FEFEFKFKFEFEFKFK-c | II | (SEQ ID NO: 14) |
| EFK8-II | n-FEFKFEFK-c | I | (SEQ ID NO: 15) |
| ELK16-II | n-LELELKLKLELELKLK-c | II | (SEQ ID NO: 16) |
| ELK8-II | n-LELELKLK-c | II | (SEQ ID NO: 17) |
| EAK16-II | n-AEAEAKAKAEAEAKAK-c | II | (SEQ ID NO: 18) |
| EAK12 | n-AEAEAEAEAKAK-c | IV/II | (SEQ ID NO: 19) |
| EAK8-II | n-AEAEAKAK-c | II | (SEQ ID NO: 20) |
| KAE16-IV | n-KAKAKAKAEAEAEAEA-c | IV | (SEQ ID NO: 21) |
| EAK16-IV | n-AEAEAEAEAKAKAKAK-c | IV | (SEQ ID NO: 22) |
| RAD16-IV | n-RARARARADADADADA-c | IV | (SEQ ID NO: 23) |
| DAR16-IV | n-ADADADADARARARAR-c | IV | (SEQ ID NO: 24) |
| DAR16-IV* | n-DADADADARARARARA-c | IV | (SEQ ID NO: 25) |
| DAR32-IV | n-(ADADADADARARARAR)-c | IV | (SEQ ID NO: 26) |
| EHK16 | n-HEHEHKHKREHEHKHK-c | N/A | (SEQ ID NO: 27) |
| EHK8-I | n-HEHEHKHK-c | N/A | (SEQ ID NO: 28) |
| VE20* | n-VEVEVEVEVEVEVEVEVEVE-c | N/A | (SEQ ID NO: 29) |
| RF20* | n-RFRFRFRFRERFRFRFRFRF-c | N/A | (SEQ ID NO: 30) |

N/A denotes not applicable
*These peptides form a β-sheet when incubated in a solution containing NaCl, however they have not been observed to self-assemble to form macroscopic structures.

The list presented in Table 1 is representative rather than exclusive. Other self-assembling peptides may be generated, e.g., by changing the amino acid sequence of any self-assembling peptide by a single amino acid residue or by multiple amino acid residues. To increase the mechanical strength of the structures, if desired, cysteines may be incorporated into the peptides to allow the formation of disulfide bonds, or residues with aromatic rings may be incorporated and cross-linked by exposure to UV light. The in vivo half-life of the structures may also be modulated by the incorporation of protease cleavage sites into the structure, allowing it to be enzymatically degraded. Combinations of any of the above alterations may also be made to the same peptide structure. Formation of cross-links by adding biotin to the peptides and then cross-linking by addition of avidin may also be used and may be a preferable approach.

The peptides may include L-amino acids, D-amino acids, natural amino acids, non-natural amino acids, or a combination thereof. If L-amino acids are present in the scaffold, degradation produces amino acids that may be reused by the host tissue. The fact that the basic monomeric subunit of the peptides in this embodiment of the invention, i.e., L-amino acids, occurs naturally within the body distinguishes this class of compounds from numerous other biocompatible substances and may offer unique advantages. The peptides may be chemically synthesized or purified from natural or recombinant sources, and the amino- and carboxy-termini of the peptides may be protected or not protected. The peptide scaffold may be formed from one or more distinct molecular species of peptides which are complementary and structurally compatible with each other. Peptides containing mismatched pairs, such as the repulsive pairing of two similarly charged residues from adjacent peptides, may also form structures if the disruptive force is dominated by stabilizing interactions between the peptides. Peptide scaffolds may also be referred to herein as peptide hydrogels or peptide hydrogel scaffolds.

Peptides capable of being cross-linked may be synthesized using standard f-moc chemistry and purified using high pressure liquid chromatography. The formation of a peptide scaffold may be initiated by the addition of ions or salts thereof as described herein. Hydrophobic residues with aromatic side chains may be cross-linked by exposure to UV irradiation. The extent of the cross-linking may be precisely controlled by the predetermined length of exposure to UV light and the predetermined peptide concentration. The extent of cross-linking may be determined by light scattering, gel filtration, or scanning electron microscopy using standard methods. Furthermore, the extent of cross-linking may also be examined by HPLC or mass spectrometry analysis of the structure after digestion with a protease, such as matrix metalloproteases. Material strength may be determined before and after cross-linking.

If desired, the peptide scaffolds formed from any of the above peptides may be characterized using various biophysical and optical techniques, such as circular dichroism (CD), dynamic light scattering, Fourier transform infrared (FTIR), atomic force microscopy (ATM), scanning electron microscopy (SEM), and transmission electron microscopy (TEM) [32, 37-39]. For example, biophysical methods may be used to determine the degree of beta-sheet secondary structure in the peptide scaffold. Additionally, filament and pore size, fiber diameter, length, elasticity, and volume fraction may be determined using quantitative image analysis of scanning and transmission electron microscopy. The scaffolds may also be examined using several standard mechanical testing techniques to measure the extent of swelling, the effect of pH and ion concentration on scaffold formation, the level of hydration under various conditions, and the tensile strength. These methods allow one of ordinary skill in the art to determine which of the various modifications and additions to the peptides described below are suitable for use in the methods of the invention.

IV. Model for Evaluation of Nerve Regeneration in the CNS

The experiments of Aguayo and co-workers [1, 2], using peripheral nerve segments taken from an animal's leg and transplanted into the CNS revealed that many CNS axons that will not regenerate after being transected in the adult animal will extend axons into the peripheral nerve (PN). A few years after the discovery that the optic tract of newborn hamsters will regenerate if transected during the first 3 days of postnatal life, in which axons grew around the site of injury [3], So and Aguayo in Montreal developed a new model for the study of CNS regeneration in adults. A long segment of sciatic nerve was used as a bridge from the back of the eye, where it was sutured after complete severance of the optic nerve, to the midbrain tectum (superior colliculus, SC) [4]. Further studies using this approach have been conducted in several laboratories. Many axons have been found to reconnect to the SC, especially when retinal ganglion cell (RGC) survival is enhanced with growth factor treatment [5-8]. Axon regeneration may be traced using immunohistochemical techniques. Since the nerve bodies are present in the retina, presence of tracer at sites distal to a site of injury must represent axon regeneration from a location (the retina) proximal to the site of injury. Some return of function has also been found, with unlearned and learned responses to presence or absence of light [7] [9] [10]. Electrophysiological recordings in such hamsters have provided evidence of functional connections [1, 11-13] although the amount of topographic organization has been found to be very limited [14]. Morphology of single regenerated axons has been described, revealing abnormally compact end arbors, but these arbors have a full complement of synapses [15, 16].

The inventors have previously demonstrated some recovery of visual orienting capability in hamsters in which the only connection from the eyes is through one long peripheral nerve (PN) (sciatic) bridge [17, 18]. This result depended on waiting a very long time for the functional regeneration to occur (1.5 years or more), but it demonstrated that functional recovery can occur and can be effectively evaluated.

Other workers have tried using shorter PN bridges over the site of a transected optic tract near the rostral border of the SC [19]. In these experiments, only a small number of regenerating axons were found to grow through the bridge. However, the inventors have improved this paradigm using adult hamsters, with a demonstration of fairly rapid and substantial recovery of visually elicited orienting movements [18]. After the surgery in 3-wk old hamsters, the anatomical and behavioral recovery was extensive, and the animals appeared to be suffer little, if any, deficit. Even with surgery at age 5.5 months, considerable recovery has been found, with a very substantial quantity of regeneration of the retinotectal projection [18]. These findings demonstrate that the optic tract regeneration model is appropriate for evaluating compositions and methods designed to facilitate neural tissue regeneration in vivo. As described herein, the model has been used to demonstrate anatomic and behavioral recovery in hamsters treated with SAP.

V. Methods and Compositions of the Invention

A. Self-Assembling Peptides as Materials for Nerve Regeneration

The inventors have identified the following criteria that are important for development of an ideal material for neural tissue regeneration: (1) building blocks are derived from molecules normally found within the host, (2) basic units are amenable to design and modification in order to achieve specific needs, (3) controlled rate of biodegradation, (4) promotion of cell-substrate interactions, (5) minimal or no cytotoxicity, (6) minimal or no elicitation of immune responses and inflammation, (7) easy and scaleable material production, purification and processing, (8) readily transportable, (9) very high water content and compatibility with aqueous solutions and physiological conditions, (10) ability to integrate with the in-vivo environment, (11) material is small enough to interact with the glycosolation of the surrounding cells. Without wishing to be bound by any theory or to limit the invention in any way, it is believed that the materials described herein attain or come close to attaining these goals.

Figure 9:
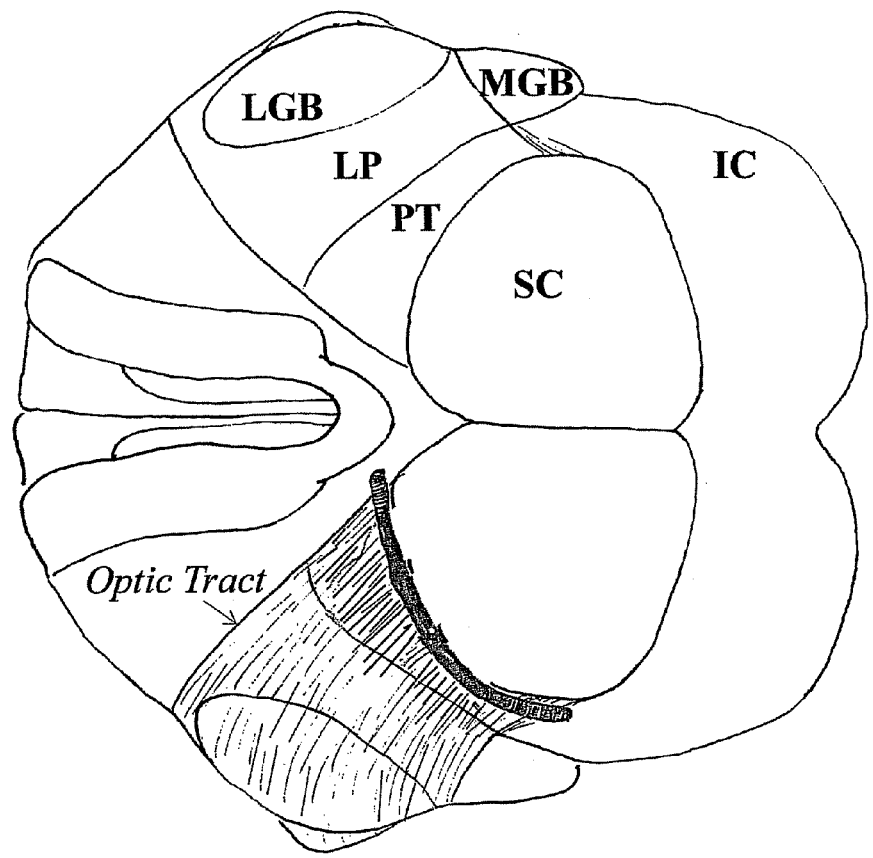
FIG. 9 is a dorsal view reconstruction of the adult hamster brain depicting the lesion of the brachium of the SC (thick line). The lesion site also indicate the location of the SAP injection. IC=inferior colliculus, LGB=lateral geniculate body, LP=lateral posterior nucleus, MGB=medial geniculate body, PT=pretectal area.
Figure 10:
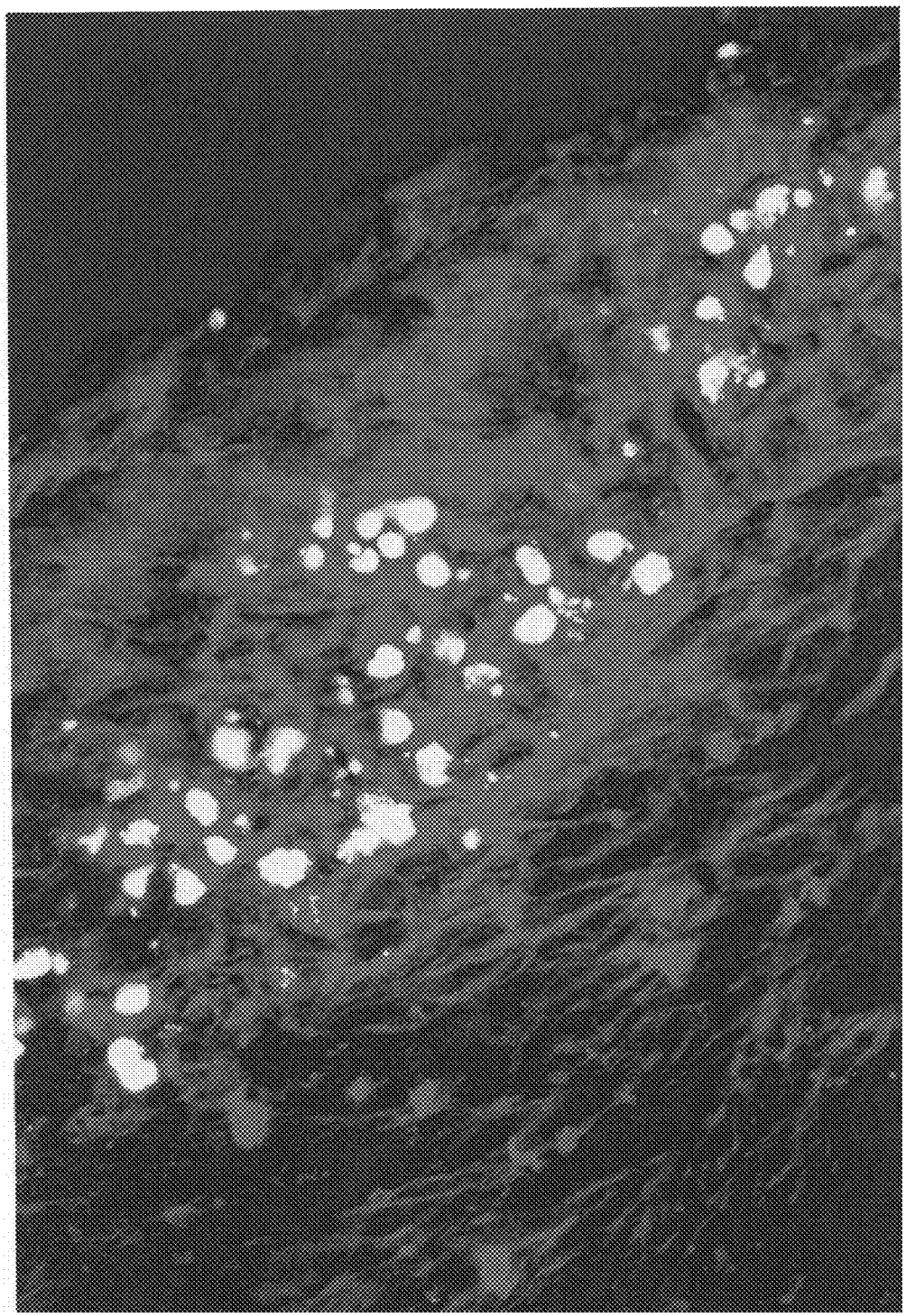
FIG. 10 is a fluorescence microscopy image of a parasagittal section of the dorsal midbrain of a hamster. Rostral is left and caudual is right. The section is from an 8 month old hamster and was taken 2 months following injection of 10 μl of 1% SAP RAD16-I into a lesion that transected the brachium of the SC. The bright yellow in the middle of the picture that extends from the lower left to the upper right is in the middle of the lesion site. Retinal projections show as gray in this Figure.
Figure 11:
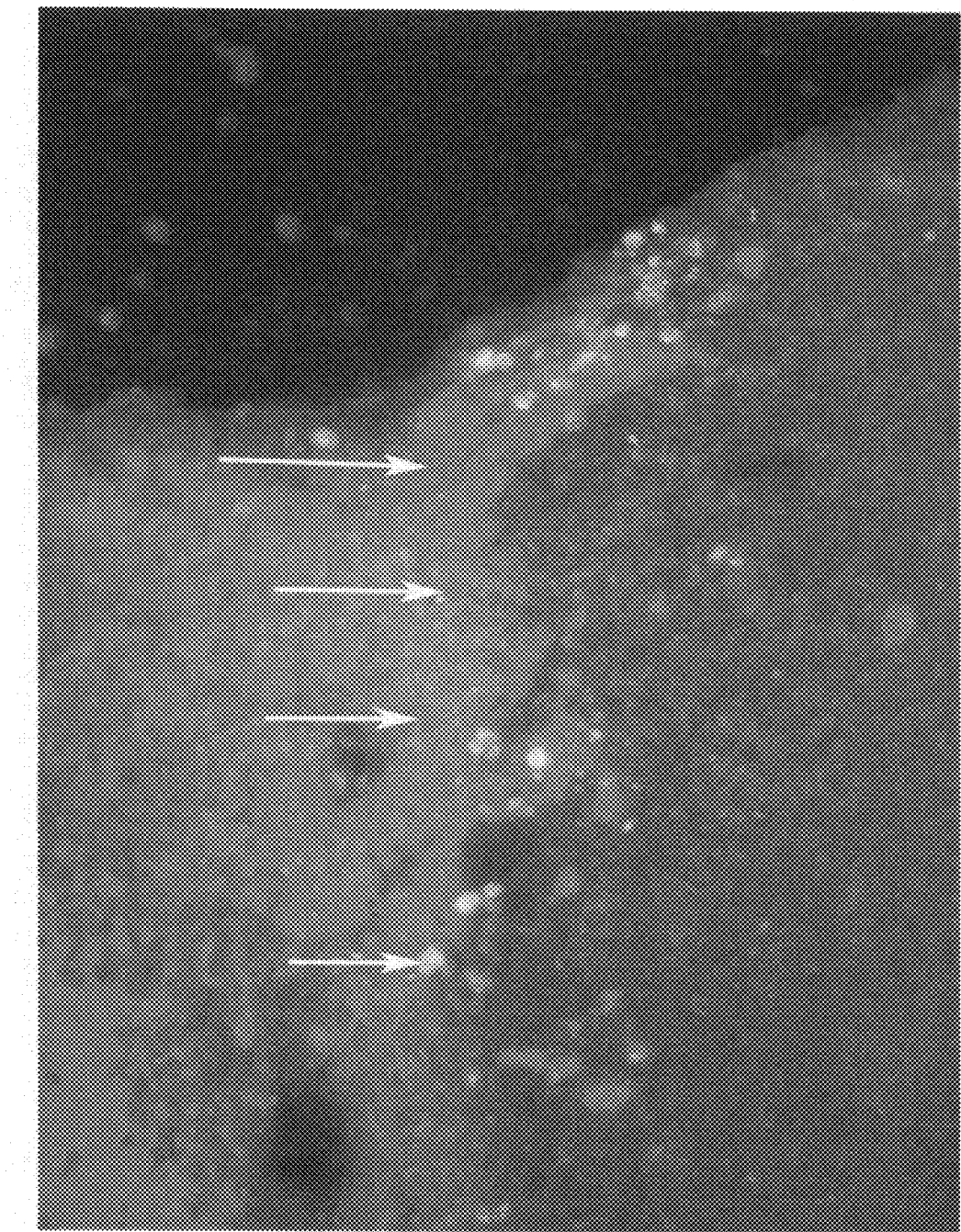
FIG. 11 is a parasagittal section of the dorsal midbrain of a hamster. Rostral is left and caudual is right. The section is from an 8 month old hamster and was taken 2 months following injection of 10 μl of 1% SAP RAD16-I into a lesion that transected the brachium of the SC. The lesion site extends from top of the picture to the bottom in the middle of the picture. White arrows indicate the middle of the lesion. Retinal projections show as gray in this Figure. This figure was taken at lower magnification than FIG. 11 and thus shows healing of the lesion over a larger scale. The site of the cut is essentially indistinguishable from the surrounding unlesioned tissue.

As described in further detail in the examples, when introduced into a site of injury in the CNS in the animal model described above, self-assembling peptides such as those described in Section II above assembled into a scaffold that provided a permissive environment in which nerve regeneration occurred. Young animals were subjected to a surgically created injury in the brain that severed axons in the optic tract. A solution containing a self-assembling peptide (RADA16-I) was then injected into the site of the lesion. Self-assembly of the peptides to form a peptide scaffold was induced by ions that were present in the CSF. Axons located proximally to the site of injury (in the retina) grew to partially re-innervate a structure (the superior colliculus) present at a location distal to the injury (Example 1). In another set of experiments (Example 2), adult hamsters were subjected to a surgically created injury in the brain that severed axons in the brachium of the superior colliculus, resulting in blindness. FIG. 9 is a schematic diagram showing the site of the lesion. A solution containing a self-assembling peptide (RADA16-I) was injected into the site of the lesion at the time of surgery. Self-assembly of the peptides to form a peptide scaffold was induced by ions that were present in the CSF. Axons located proximally to the site of injury (in the retina) grew to partially re-innervate a structure (the superior colliculus) present at a location distal to the injury, as shown in FIGS. 10 and 11. In addition, functional recovery (restoration of response to a visual stimulus), was demonstrated as described in Example 2 and shown in FIG. 12.

It is believed that the experiments described herein represent the first demonstration that introduction of a nanostructured material at a site of injury in the CNS can support successful axon regrowth across the site of injury. Presence of the SAP appears to permit the two faces of an injury to become reapposed, allowing separated tissues to knit together. Presence of the SAP appears to prevent the formation or deposition of inhibitory scar tissue while not preventing, and perhaps directly stimulating, the extension of nerve cell processes. Thus, the SAP was shown to offer a new means of ameliorating tissue disruptions caused by traumatic injury to the CNS, allowing regrowth of young axons that are believed to have regenerative potential as well as adult axons whose regeneration potential has heretofore been believed to be extremely limited or nonexistent.

In general, any of the SAPs described above may be used in the practice of the invention. However, it is possible that certain of the SAPs will possess uniquely favorable characteristics for nerve regeneration while others may prove less favorable. These properties may be evaluated as described in the examples. The SAPs may be introduced at a site of injury by injection, prior to self-assembly, whereupon they self-assemble in vivo. They may also be assembled in vitro and provided at the site of injury in any of a variety of ways, e.g., by injection from a needle, by extrusion from a syringe, by deposition of dry powder, or by direct deposition of a preformed scaffold. The scaffold may, if desired, be shaped into an elongated or tubular structure. In addition, the SAPs may be incorporated into a composite structure. For example, an outer sheath comprised of a different biocompatible material may be filled with an SAP gel. The outer sheath may resemble, for example, nerve guides or cuffs such as those used in the art to facilitate nerve regeneration [see 86 for a review that describes a number of such devices and lists references.]

B. Self-Assembling Peptide Scaffolds Incorporating Additional Substances

In various embodiments of the invention one or more additional substances is added to the peptide scaffold either prior to or following self-assembly. The substance may serve any of a number of purposes, including, but not limited to, those described below. In certain embodiments of the invention neural tissue contacts the substance as it extends or grows into the area occupied by the peptide scaffold. In certain embodiments of the invention the substance is released from the scaffold, e.g., by diffusion, or by release from the scaffold as it degrades over time. The peptide concentration and features such as cross-linking may be selected to provide a desired rate of degradation and release of the substance. The substance may contact neural tissue at or near the site of injury and/or may enter the bloodstream and travel to more distant locations. It is noted that in addition to the various substances described below, which are selected primarily based on their useful properties for enhancing neural tissue regeneration, various other biologically active substances can be incorporated into the scaffold. A biologically active substance is any substance that can, either directly or indirectly, produce a biological effect, preferably a substance that can confer a therapeutic benefit. Such substances include, but are not limited to, antibiotics or antifungal agents to treat or reduce the risk of infection, chemotherapeutic agents to treat tumors, anti-inflammatory agents, immunosuppressive agents, chemotactic agents, etc. In general, any biomolecule (e.g., protein, lipid, nucleic acid, etc.), other organic molecule (e.g., a small molecule) or inorganic molecule (e.g., a mineral), can be included in the composition. The invention therefore provides a composition comprising a nanoscale structured material or a precursor thereof and an additional active substance. In certain preferred embodiments of the invention the composition comprises self-assembling peptides, wherein the peptides are amphiphilic peptides that comprise substantially equal proportions of hydrophobic and hydrophilic amino acids and are complementary and structurally compatible. The invention provides compositions comprising the precursor components of the nanoscale structured material (e.g., self-assembling peptides or a solution thereof that have not yet undergone assembly) and the active substance. Preferably the peptides self-assemble to form a beta-sheet macroscopic scaffold. Active substances can be provided at any suitable concentration and in any suitable amount, e.g., in the microgram or milligram range, or greater.

1. Regeneration Promoting Factors

A number of substances that are known to increase neuron survival and rate of neuronal growth have been found. Such substances are referred to herein as neural regeneration-promoting factors (RPF). RPFs may usefully be divided into extrinsic and intrinsic factors. Extrinsic RPFs are generally factors that are not by neurons themselves but which act on them to enhance regeneration. Many of these factors were identified as endogenously occurring molecules (e.g., peptides) that bind to the cell or otherwise influence the cell from the extracellular environment, e.g., by triggering a signaling cascade or blocking a program that may send a cell down the apoptotic pathway. One example of a such a factor of use in the present invention is ciliary neurotrophic factor (CNTF), a factor used to preserve (i.e., maintain viability of) neurons. With complete optic nerve section in rats, the grafting of a PN segment to the optic nerve stump does not prevent a massive loss of retinal ganglion cells—less than 10% are reported to survive following this procedure [54-57]. Trying to slow and reduce this cell death has been a major goal for investigators using this or other paradigms for inducing CNS axon regrowth. Positive results have been reported using various extrinsic factors, primarily CNTF [58-60].

Additional RPFs of use in the present invention include a family of neurotrophic factors referred to as neurotrophins. These include nerve growth factor (NGF), brain derived neurotrophic factor (BDNF), neurotrophin-3 (NT-3), neurotrophin-4/5 (NT-4/5), neurturin (NTN), persephin (PSP), and artemin (ART) [86, 99, 100]. Other factors that are known to influence nerve regeneration include glial cell derived growth factor (GDNF), and acidic and basic fibroblast growth factor (aFGF, bFGF). Particular factors have been shown to enhance regeneration in various contexts within the CNS and/or PNS [see 86 and references therein]. Additional factors that may aid in nerve regeneration include adhesion molecules such as L1, NCAM, and N-cadherin, molecules that influence axon guidance and pathfinding (e.g., semaphorins, slits, netrins, ephrins, etc.), chemotactic factors, synaptogenic factors (e.g., agrin, laminin, and ARIA). These molecules may either be provided exogenously, e.g., as a component of a SAP scaffold, or their expression may be upregulated, as described below. RPFs (or other active substances) can be provided at concentrations that have been shown in the art to promote nerve regeneration or any other desired effect. Growth factors are typically used at concentrations ranging between about 1 fg/ml to 1 mg/ml. Frequently growth factors are used at concentrations in the low nanomolar range, e.g., 1-10 nM. In certain embodiments of the invention growth factors are used at concentrations that are not typically used in the prior art or that are not typically found in vivo under normal conditions. For example, growth factors may be used at concentrations that are 5 fold greater, 10 fold greater, 20 fold greater, 100 fold greater, etc., than is typically required to produce effects or than typically occurs in vivo. Titration experiments can be performed to determine the optimal concentration of a particular agent, such as a growth factor, depending upon the particular effects desired. Factors may be added in purified form or as components of a complex biological mixture such as serum. Factors that promote cell proliferation may be referred to as proliferation agents.

Another approach to increasing the regeneration capacity of nerves is to alter the expression of a variety of regeneration-associated genes, genes that encode components of the neuronal cytoskeleton (e.g., actin, gelsolin, or other actin-associated proteins), and/or genes that encode anti-apoptosis factors. RPFs that are produced by neurons themselves may be referred to as intrinsic factors. Regeneration-associated genes are expressed transiently during development of the nervous system and are typically not expressed in healthy adult nerves. However, upon injury to peripheral nerves some of these genes are reexpressed, and such reexpression is believed to be important for successful regeneration. Its absence may be part of the reason why regeneration does not occur in the injured CNS. Regeneration-associated genes include GAP-43 and CAP-23 [see 86 and references therein]. It has been reported that mutant mice that overexpress two proteins found in axonal endings, GAP-43 and CAP-23, show a considerable enhancement of regeneration of transected dorsal column axons in a PN bridge [79].

The great decrease in regenerative capacity of the mammalian optic nerve has been found to be caused by changes intrinsic to the retinal cells [69]. It was found that down-regulation of Bcl-2 is a major component of this change in retinal ganglion cells [45]. This gene appears to play some as yet unidentified role in neurite elongation, in addition to its better known role in preventing apoptotic cell death, e.g., the neuronal death due to inadequate uptake of neurotrophic factors. In addition, overexpression of Bcl-2 protein in transgenic mice can greatly promote regenerative capacity of retinofugal axons transected in the midbrain [45]. Such experiments have demonstrated the great importance of intrinsic factors in neurons for their ability to regenerate. Therefore, use of methods to produce an increase in intrinsic factors like Bcl-2, GAP-43, and CAP-23 may prevent much of the cell death that would curb regenerative axon growth, and would also promote axon elongation. Increasing production or release of other anti-apoptotic substances or, conversely, decreasing expression of pro-apoptotic substances (either produced by neurons or other cell types), may also be useful.

Gene therapy techniques may be used to increase expression of genes whose products enhance regeneration. Gene therapy encompasses delivery of nucleic acids comprising templates for synthesis of a molecule of interest (e.g., a therapeutic polypeptide or nucleic acid) to a cell of interest. The nucleic acid (or a nucleic acid derived from the nucleic acid as, for example, by reverse transcription) may be incorporated into the genome of the cell or remain permanently in the cell as an episome. However, gene therapy also encompasses delivery of nucleic acids that do not integrate or remain permanently in the cell to which they are delivered. Such approaches permit temporary or transient synthesis of a molecule of interest.

"Naked" nucleic acids, vectors (e.g., gene therapy vectors) and vehicles that provide nucleic acids comprising templates for synthesis of nucleic acids and proteins may be incorporated into SAP scaffolds, from which they may be taken up by cells at or near a site of injury. Preferably the nucleic acid includes a coding sequence for a molecule to be expressed in a cell of interest and also includes appropriate expression signals, e.g., promoters, terminators, etc., to ensure proper expression, operably linked to the coding sequence. The molecule to be expressed can be an RNA that is then translated into a protein, or a therapeutic nucleic acid such as a short interfering RNA, antisense RNA, ribozyme, etc. In certain embodiments of the invention the expression signal(s) are cell type specific, so that the gene will only be expressed in cells of a particular cell type, e.g., neurons. A wide variety of cell type specific proteins are known in the art. For example, nestin is an intermediate filament protein expressed in neuroepithelial neuronal precursor stem cells, and its expression decreases with neuronal maturation [87]. Nestin is considered a marker for immature neurons, and nestin-positive cells can differentiate into either neurons or glia. NeuN is a neuron-specific marker expressed in postmitotic cells [88]. Glial fibrillarary acidic protein (GFAP) is a classic glial astrocyte marker. Beta III tubulin is another neuron-specific protein. Promoters from any of these cell type specific genes, or others known in the art, may be used to selectively express a gene of interest in the cell type in which the cell type specific gene is normally expressed.

In general, either viral or non-viral vectors or vehicles may be used. In certain embodiments of the invention the vector is a viral vector that is able to infect neurons. For example, herpes virus, adenovirus, adeno-associated virus, retroviruses, or lentiviruses may be used. It may be preferable to avoid the use of intact viruses in delivering templates to cells. Thus it may be preferable to deliver nucleic acid (e.g., DNA) vectors or linear nucleic acid molecules. These vectors may, but need not, include viral sequences such as long terminal repeats, etc. Any of a wide variety of agents useful for transfection may be used to enhance uptake of nucleic acids by cells. Such agents include a wide variety of cationic polymers and modified cationic polymers, lipids, etc. Cationic polymers are known to spontaneously bind to and condense nucleic acids such as DNA into nanoparticles. For example, naturally occurring proteins, peptides, or derivatives thereof have been used. Synthetic cationic polymers such as polyethylenimine (PEI), polylysine (PLL), polyarginine (PLA), polyhistidine, etc., are also known to condense DNA and are useful delivery vehicles. U.S. Pat. No. 6,013,240 and PCT application WO9602655 provide further information on PEI Cationic polymers modified by addition of groups such as acyl, succinyl, acetyl, or imidazole groups, e.g., to reduce cytotoxicity, can be used. Dendrimers can also be used. See [70, 80, and 89-91] for discussion of and approaches for gene therapy. Cell-type specific targeting ligands (e.g., the nontoxic neuronal-specific fragment C of tetanus toxin), or an antibody that specifically binds to a molecule expressed on a cell type of interest may be attached to a gene therapy delivery agent to allow transfection of only certain cell types. In general, the nucleic acid and any appropriate gene therapy delivery agent (e.g., a cationic polymer) may be incorporated into the scaffold in any of the ways discussed below.

The invention therefore provides a composition comprising a nanoscale structured material and a neural regeneration promoting factor. In certain preferred embodiments of the invention the composition comprises self-assembling peptides, wherein the peptides are amphiphilic peptides that comprise substantially equal proportions of hydrophobic and hydrophilic amino acids and are complementary and structurally compatible. The invention provides compositions comprising the precursor components of the nanoscale structured material (e.g., self-assembling peptides or a solution thereof that have not yet undergone self-assembly) and the neural regeneration promoting factor. Preferably the peptides self-assemble to form a beta-sheet macroscopic scaffold. Particular extrinsic RPFs that may be incorporated into the scaffold include, but are not limited to, CNTF, NGF, BDNF, NT-3, NT-4/5, GDNF, aFGF, and bFGF. Particular intrinsic RPFs that may be incorporated into the scaffold include, but are not limited to, nucleic acids that provide templates for synthesis of a regeneration enhancing protein. Particular regeneration enhancing proteins include, but are not limited to, GAP-43, CAP-23, and Bcl-2. Additional RPFs that may be incorporated into the scaffold include lithium (which has been shown to have neuroprotective properties and also upregulates genes that are present during early development as well as certain genes that are believed to be critical for neuronal survival [71-74]), laminin, agrin, acetylcholine receptor inducing activity protein (ARIA), L1, NCAM, and N-cadherin, semaphorins, slits, netrins, and ephrins.

2. Substances that Counteract Inhibitory Molecules

One of the greatest challenges that faces efforts to enhance regeneration and repair in the CNS is the development of scar tissue, which typically results in the formation of a nonpermissive environment that may inhibit axon growth and/or myelination [86]. Scarring involves a variety of cell types, including macrophages, microglia, oligodendrocytes, and astrocytes. Various noncellular components of a scar typically include myelin-associated molecules (e.g., Nogo, myelin associated glycoprotein, oligodendrocyte-myelin glycoprotein), chondroitin sulfate proteoglycans, collagens, etc. Certain of these molecules have been shown to inhibit regeneration of neural tissue. For example, it has been shown that oligodendrocyte myelin inhibits nerve regeneration, and antibodies that bind to the myelin protein NI-35 can block this inhibition [86 and references therein]. Antibodies that bind to growth inhibitory molecules, e.g., molecules found in of scar tissue that forms after injury to neural tissue, including, but not limited to, Nogo, myelin associated glycoprotein, oligodendrocyte-myelin glycoprotein may be incorporated into the peptide scaffold. Such antibodies may block interaction between the inhibitory molecule and a neural tissue cell, e.g., a neuron or glial cell. A variety of enzymes that degrade growth inhibitory molecules are known. For example, chondroitinase ABC degrades chondroitin sulfate proteoglycan side chains, which are upregulated following spinal cord injury and inhibit axonal growth. Enzymes including, but not limited to, chondroitinase ABC or any other enzyme that degrades chondroitin sulfate proteoglycan side chains can be incorporated into the peptide scaffold.

Another approach to decrease the amount of an inhibitory molecule (e.g., an inhibitory molecule produced by a cell at or near a site of injury) is to take advantage of the phenomenon of RNA-mediated interference (RNAi) to reduce expression of a transcript that encodes the inhibitory molecule [92-95]. Briefly, it has been found that the presence of a short double-stranded RNA molecule referred to as a short interfering RNA (siRNA), one strand of which is substantially complementary to a transcript present in a cell (the target transcript) within a cell results in inhibition of expression of the target transcript. The mechanism typically involves degradation of the transcript by intracellar machinery that cleaves RNA (although translational inhibition can also occur). Short hairpin RNAs are single-stranded RNA molecules that include a stem (formed by self-hybridization of two complementary portions of the RNA) and a loop, which can be processed intracellularly into siRNA. SiRNA and shRNA has been demonstrated to inhibit expression of target transcripts in mammalian cells both in tissue culture and in vivo. An siRNA or shRNA whose presence within a cell leads to inhibition of expression of a transcript by RNA interference, whether by causing degradation of the transcript or by causing translational repression, is said to be targeted to the transcript. SiRNAs or shRNAs targeted to a transcript that encodes an inhibitory molecule can be incorporated into the scaffold. Transfection enhancing agents can also be included to increase uptake of the siRNA or shRNA. Alternatively, a vector that provides a template for intracellular synthesis of one or more RNAs that hybridize to each other or self-hybridize to form an siRNA or shRNA can be incorporated into the scaffold for delivery to cells at or near the site of injury.

Any substance that acts to counteract the effect of a molecule that is inhibitory for neural regeneration or repair, whether by causing degradation, sequestering, reducing expression, or blocking interaction of the molecule with a cell will be said to counteract the inhibitory molecule. It is also noted that the SAP itself may serve to sequester inhibitory molecules. The invention therefore provides a composition comprising a nanoscale structured material and a substance that counteracts a molecule that inhibits regeneration or growth of neural tissue. In certain preferred embodiments of the invention the composition comprises self-assembling peptides, wherein the peptides are amphiphilic peptides that comprise substantially equal proportions of hydrophobic and hydrophilic amino acids and are complementary and structurally compatible. The invention provides compositions comprising the precursor components of the nanoscale structured material (e.g., self-assembling peptides or a solution thereof that have not yet undergone assembly) and the substance that counteracts a molecule that inhibits regeneration or growth of neural tissue. Preferably the peptides self-assemble to form a beta-sheet macroscopic scaffold.

3. Cells

As described above, repair and regeneration of neural tissue can be enhanced by supplying regeneration promoting factors such as neurotrophic factors, cell adhesion molecules, integrins, etc. One way to provide such molecules (or others), is to deliver cells at the site of injury. The cells may produce molecules that promote regeneration or otherwise contribute to producing an environment permissive for regeneration. Schwann cells, CNS glial cells, macrophages, and olfactory ensheathing cells are among the cells that may be useful in this regard [86 and references therein]. In addition, various progenitor cells, e.g., neural progenitor cells, glial progenitor cells, and/or stem cells, may also be useful. The cells may or may not produce a regeneration promoting factor. Any of these cell types may be incorporated into the scaffold. In addition, any of these cell types (or others) can be genetically modified, e.g., to increase the production of a regeneration promoting factor, prior to incorporation into the scaffold. The cell(s) may be autologous or non-autologous. They may be allogeneic or non-allogeneic. They may be from the same species as the subject into which they are introduced or from a different species. They may be fetal or adult. In certain embodiments of the invention the cells are neural cells. In certain embodiments of the invention the cells are introduced to treat a disease such as Parkinson's disease [98]. For example, the cells can be dopaminergic neurons.

The invention therefore provides a composition comprising a nanoscale structured material and a cell. In general, the composition will comprise a population of cells. In certain preferred embodiments of the invention the composition comprises self-assembling peptides, wherein the peptides are amphiphilic peptides that comprise substantially equal proportions of hydrophobic and hydrophilic amino acids and are complementary and structurally compatible. The invention provides compositions comprising the precursor components of the nanoscale structured material (e.g., self-assembling peptides or a solution thereof that have not yet undergone assembly) and the cell. Preferably the peptides self-assemble to form a beta-sheet macroscopic scaffold.

4. Methods for Incorporation of Substances into SAP Scaffold

In general, RPFs, blocking agents, cells, etc. may be incorporated into the peptide scaffolds in a number of different ways. For purposes of description any such molecule or cell is referred to in this section as a "substance". Generally incorporation may be via a bond such as a covalent bond, ionic bond, etc., or may be by physical encapsulation. Formation of the SAP scaffold may be divided into four stages, as follows:

Stage 1. Select the peptides and mix at the desired concentration.

Stage 2. Introduce the material at the site of injury (e.g., by injection). A specific pattern of introduction may be employed.

Stage 3. Self-assembly of peptide.

Stage 4. Post assembly deposition of RPFs.

Stage 4 is only necessary in the case of scaffolds that incorporate additional substance(s), where the incorporation occurs after introduction of the peptides at the site of injury. It will be appreciated that stages 2 and 3 can take place in the opposite order, i.e., the scaffold can be assembled in vitro prior to introduction at a site of injury. In general, the stage at which incorporation takes place may be selected based on the nature and/or chemical makeup of the substance. Multiple substances incorporated in each step or combination of steps. Incorporation at the various stages is discussed below, roughly in reverse order of degree to which incorporation may affect or involve the process of assembly of the scaffold.

Incorporation at Stage 4: Perhaps the most expedient way of incorporating substances into the scaffold is to deposit the SAP as described above and then deposit the additional substance (e.g., as a solution) at stage 4 on the scaffold after self-assembly has occurred in vivo, e.g., a short period of time after introduction of the peptide at the site of injury. This method offers certain advantages, e.g., it will not perturb the peptide assembly.

Incorporation at Stage 3: The presence of ions (e.g., in the form of a salt) is necessary for the self-assembly process of the sapeptide. Certain RPFs are salts and may be able to initiate self-assembly. One example would be an aqueous solution containing LiCl (or another salt containing Li). LiCl can be added to the peptide solution shortly before introducing it at the site of injury. Li ions may then contribute to self-assembly in vivo. Alternately, LiCl may be added to the peptide solution and self-assembly allowed to occur in vitro. The assembled peptides may then be introduced at the site of injury.

Incorporation at Stage 2: Co-deposition. The sapeptide and the substance(s) may be co-loaded in a device used to introduce the scaffold material at the site of injury, e.g., a syringe, and then extruded.

Incorporation at Stage 1: Modification of the peptide and use of other peptides. Some of the RPFs include building blocks for the neuron during its elongation stage, e.g., precursors or substrates for synthesis of an endogenous molecule such as a protein or peptide, nucleic acid, carbohydrate, lipid, etc. For example, the substance may be a nucleoside such as inosine, which can be used in the synthesis of nucleic acids. Such substances, which are used in the normal metabolic and/or anabolic processes of the cell, will be referred to collectively as nutrients. One example is CDP-Choline. Since choline is used by every cell in the body and there are choline-specific transporters, simple deposition on the sapeptide may not be optimal since the molecule may simply diffuse away. An approach to address this issue is to cause incorporation of the substance into the structure of the sapeptide or to tether the substance to the scaffold. The amount of choline can be adjusted depending, for example, on the extent of damage to neural tissue and the growth required for complete regeneration. Also, it is noted that choline is one of the primary precursors for the production of the neurotransmitter acetylcholine. In general, in certain embodiments of the invention the substance is a precursor of or substrate for synthesis of a neurotransmitter. It is noted that the peptides themselves comprise amino acids, which may serve as substrates for synthesis of proteins or peptides by neural cells. In certain embodiments of the invention the substance is a nutrient other than an amino acid provided by the peptides themselves.

As the scaffold degrades over time neural tissue, e.g., axons and oligodendrocytes, will be provided with material to allow and enhance regeneration. In general, peptides may be modified in accordance with methods described in copending U.S. patent application entitled "Self-Assembling Peptides Incorporating Modifications", Ser. No. 10/877,068, filed Jun. 25, 2004, which is incorporated herein by reference. Methods include covalent linkage and modifying the sequence of the peptide, e.g., by including particular motifs within the peptide. See Ser. No. 10/877,068 for further details, including discussion of particular motifs that may enhance neural regeneration or repair.

Simply mixing the sapeptide and the substance prior to initiation of self-assembly will typically result in encapsulation of the substance by the peptide. Combinations of the foregoing may be used. For example, the overall process may include initial addition of a stage 1 modification, e.g., CDP-choline, to the sapeptide. Then a molecule LiCl can be used to cause the self-assembly of the sapeptide prior to or following introduction of the sapeptide at the site of injury (stage 3). Both the sapeptide and an RPF can be delivered in a pattern that will modify the direction of growth and/or enhance the growth rate, etc., of the neurons. Introduction of another substance such as a growth factor (at stage 4) could be used to promote axon sprouting. In certain embodiments of the invention molecules to be incorporated into the scaffold may be encapsulated in microparticles or nanoparticles, e.g., polymeric microparticles or nanoparticles, which are then themselves incorporated into the scaffold. Preferably the polymers or other materials used for formation of such drug delivery devices are biocompatible. Certain preferred polymers are biodegradable. Suitable polymers include, but are not limited to, poly(lactic-co-glycolic acid), polyanhydrides, ethylene vinyl acetate, polyglycolic acid, chitosan, polyorthoesters, polyethers, polylactic acid, and poly (beta amino esters). Peptides, proteins such as collagen, and dendrimers (e.g., PAMAM dendrimers) can also be used. Methods for making polymeric microparticles and nanoparticles and/or for making polymer/nucleic acid complexes, are described in U.S. patent application Ser. No. 10/446,444. It will be appreciated that a variety of different substances other than the substances discussed above may be incorporated In general, a variety of devices may be used to introduce the scaffold material at or in the vicinity of a site of injury. The composition may be locally delivered at or near a site of injury or degeneration by injection (e.g., using needle and syringe), catheter, cannula, etc. The composition may be delivered under imaging guidance, e.g., stereotactic guidance. A composition can also be administered locally to its intended target tissue during surgery, in which case it can, if liquid or gel, be delivered using a syringe or poured from a suitable vessel. Alternately, a material can be wetted with the composition and then used to apply a composition to an area of tissue.

Delivery via a syringe is one convenient technique. Multi-port syringes may be used, in which case each port may contain a different sapeptide/substance combination, or varying concentrations of sapeptide/substance. In this manner directional deposition of scaffold material can be achieved. Gradients of substances can be introduced. Any suitable pattern can be employed, depending upon the direction in which neural tissue regeneration is desired and the particular stratification desired.

VI. Therapeutic Applications

In general, the methods and compositions of the invention are useful in any situation involving injury to neural tissue. Such injury may occur as a result of surgery, trauma, stroke, tumor, neurodegenerative disease, or other diseases or conditions. The injury may involve complete or incomplete transection of axons. The injury may, but need not, involve death of neural cells. The methods and compositions are useful to restore structural and/or functional integrity to the neural tissue, i.e., to aid in restoring the tissue to the functional or structural condition that existed prior to the injury. Certain injuries may result in physical barriers that can impede regeneration or repair of neural tissue. Such barriers may include areas of necrosis, cavitation, or scar tissue formation. In certain embodiments of the invention introducing the materials described herein at a site of injury allows axon growth from a location proximal to the site of injury or barrier to a location distal to the site of injury or barrier.

In addition, the methods and compositions of the invention are useful to promote formation of neural tissue at locations or in configurations other than those normally found in the subject. For example, if a barrier such as a scar exists, the methods and compositions of the invention may be employed to create new areas of tissue that circumvent or eliminate the barrier. New neural tissue that functionally compensates for or replaces neural tissue that has been lost (e.g., due to stroke) can be created with the aid of the methods and compositions described herein, offering the possibility of reconstructive neurosurgery, e.g., reconstructive brain surgery. The scaffolds described herein may form a bridge or guide for development of new neural tissue.

Although the applications of the invention have primarily been described in reference to regeneration of neural tissue in the CNS, it is evident that they may also be employed to enhance regeneration of nerves in the PNS, where the requirements for nerve regeneration are less demanding.

The compositions and methods of the invention are also of use for treating spinal dysfunction or damage due to any of a variety of conditions. By "spinal dysfunction or damage" is meant any condition resulting in a detrimental structural and/or functional alteration in the normal motor, sensory, and/or support functions of the spine, e.g., vertebral column (vertebrae and/or discs) and/or spinal cord. The dysfunction may result in pain either with or without an evident structural alteration or abnormality.

In particular, the compositions and methods of the invention are may be used in replacement, repair, and/or regeneration of intervertebral disc tissue, e.g., nucleus pulposus tissue. The intervertebral disc is a fibrocartilaginous disc serving as a cushion between all of the vertebrae of the spinal column. The disc consists of a nucleus (nucleus pulposus), composed primarily of proteoglycans and Type II collagen with a capacity to absorb and distribute load, and an outer, tougher annulus (annulus fibrosis) with well-organized layer of Type I collagen that serves to stabilize the motion segment. The structure and/or function of the disc may be altered by various processes including normal physiological aging, mechanical factors including trauma and repetitive stress, segmental instability of the spine, and inflammatory and biochemical factors. In the condition known as a herniated disc, the nucleus pulposus is forced through a weakened part of the disc. This results in back pain and leg pain (lumbar herniation) or neck pain and arm pain (cervical herniation) due to nerve root irritation.

Current approaches for treatment of damaged, e.g. herniated discs include intervertebral disc excision (discectomy), arthrodesis (fusion) of the spine using posterior, anterior, or combined approaches. However, treatment of back pain and functional preservation may be most effective if disc function is restored. The compositions of the invention can be used to replace or augment intervertebral disc tissue in conjunction with, or instead of, any of the foregoing procedures. The intervertebral disc tissue to be replaced or repaired may be tissue that is damaged due to trauma, during surgery, etc., or may be tissue that has degenerated, thinned, bulged, or herniated. Repair can include any aspect of anatomical or functional restoration of the condition of the intervertebral tissue to a normal condition, e.g., a conditions prior to an injury or degenerative process. Disc repair can be performed in conjunction with other aspects of spinal regeneration including, but not limited to, use of the compositions of the invention to repair and/or regenerate spinal neural tissue, i.e., spinal cord tissue and/or spinal nerve tissue.

The compositions, e.g., self-assembling peptides (either pre-assembled or in solution), can be introduced into a damaged disc space (e.g., within a region surrounded or partially surrounded by annulus fibrosis), or can be used to create an entirely new disc, which may be referred to as a replacement disc, disc implant, etc. The replacement disc may consist essentially of a composition of the invention, i.e., a nanoscale structured material such as a composition comprising self-assembling peptides as described above. The composition may optionally include one or more additional agents, e.g., a biologically active substance such as a therapeutic agent.

In certain embodiments of the invention the replacement disc includes one or more supplementary materials. For example, a composition of the invention may be used for nucleus pulpusos replacement, while a second material (either synthetic or derived from natural sources) can be used to functionally and/or structurally replace all or part of the annulus fibrosis. For example, fibrous tissue may be removed from elsewhere in a patient's body and used to replace or repair a damaged annulus fibrosis. Damaged or lost nucleus pulposus may be replaced with a composition of the invention. Natural or synthetic polymeric materials can also be used for this purpose. Metals, plastics, e.g, polyethylene, or other biocompatible materials known in the art can be used to fabricate a replacement disc. An intervertebral disc replacement may comprise an inner portion and an outer portion. The inner portion may comprise or consist essentially of self-assembling peptides. The outer portion may also comprise or consist of self-assembling peptides or may comprising or consist essentially of one or more other materials. The other material(s) may provide a greater strength or stiffness than the material(s) that comprise the inner portion. For example, a replacement disc may comprise an outer portion comprising a metal, plastic, or polymer, and an inner portion comprising a nanoscale structured material, e.g., a composition comprising self-assembling peptides. A composition of the invention may provide a nucleus pulposus implant, which may be used together with existing intervertebral disc replacement devices. Alternately, different compositions of the invention (e.g., peptide compositions of different stiffness) can be used to replace nucleus pulposus and annulus fibrosis.

Any suitable diagnostic test or combinations thereof may be used to identify a patient in need of replacement and/or repair of intervertebral disc tissue. For example, the straight-leg raising test may be used to diagnose presence of a herniated lumbar disc. Myelograms and/or imaging studies such as MRI scans are also of use.

The methods and compositions of the invention may be tested using any of a variety of animal models for injury to, or degeneration of, the nervous system or spine, e.g., intervertebral disc. One such model, involving a knife wound to the optic tract in hamsters, is described in detail herein. Other models that may be used include, but are not limited to, a rodent model of anterior ischemic optic neuropathy [96]; rodent models for thromboembolic stroke [97], etc. See also references in 86.

EXAMPLES

Example 1

SAP Peptide Scaffolds Support Neural Tissue Regeneration In Vivo

Materials and Methods

Animals and surgery. Syrian hamster pups at two days of age (P2) were anesthetized with whole-body cooling. The scalp was opened and the optic tract within the superior colliculus (SC) was completely severed with a deep knife wound through a slot cut in the cartilaginous skull, extending 1-2 mm below the surface from the midline to a point beyond the lateral margin of the SC. At surgery, 10 animals were treated by injection into the brain wound of 10 microliters of 1% SAP RADA16-I (n-RADARADARADARADA-c; SEQ ID NO: 1) prepared by dissolving peptide in sterile water. The overlying scalp was then closed with tissue glue (cyanoacrylic). The pups were returned to the cage, placed under a heat lamp, and monitored until they recovered. After recovery the hamster pups were returned to their mother. Control animals with the same lesion included 3 with isotonic saline injection (10 microliters), and 27 earlier cases with knife cuts and no injection.

Axon tracing method. Four days before the animals were sacrificed they were anesthetized with intraperitoneal injection of Valium (50 mg/kg) and Nembutal (10 mg/kg). The animals with survival times of 6, 30, and 60 days received intraocular injections of 1 µl of 1% Cholera-toxin subunit B (CT-B) conjugated with fluorescein isothiocyanate (CTB-FITC) (List Biological, Inc) into the vitreous humor of the left eye. This was accomplished with the aid of glass micropipette (tip diameter ~10 µm) attached to a General Valve Pico Spritzer as previously described [52, 53]. The subjects were then returned to their cages, under a heat lamp, and monitored until they recovered.

Histology. The animals were sacrificed with an overdose of anesthesia 4 days after the intraocular injection of CT-B and were then perfused transcardially with PBS buffer (pH 7.4) followed by 2% paraformaldehyde in 0.1M phosphate buffer (pH 7.4). The brains and eyes were removed and postfixed at 4° C. until they sank. The tissue was cut on a cryostat in 30 micron coronal sections. These sections were mounted directly on gelatin-coated slides. The mounted sections were first air dried, then washed with PBS (pH 7.4) three times at 10 min intervals, and then preblocked in PBS (pH 7.4) containing 2% Triton X-100, 2% normal rabbit serum, and 2.5% bovine serum albumin for 30 min at room temperature. The slides were then incubated with goat anti-cholaragenoid (List Biological Lab, Inc.) (1:8000 dilution)+2% Triton X-100, 2% normal rabbit serum, and 2.5% bovine serum albumin for 48 hours at room temperature. Slides were then washed in PBS (pH 7.4) for three rounds of 10 min each. Sections were incubated with fluorescent donkey anti-IgG antibody Alexa-488 (secondary antibody from Molecular Probes, Inc.) (1:200 dilution) for 1 her 30 min at room temperature in a light protected chamber. Slides were then washed in PBS (pH 7.4) 4 to 5 times at 5 min intervals. The slides were then cover-slipped with Dabco. The slides were visualized through a fluorescent microscope and pictures were taken with a Kodak DCS 620 digital camera.

Results

A tissue gap caused by deep transections of the optic tract (OT) in the midbrain can completely block the re-innervation of the superior colliculus (SC) by the retina, even when done at young ages when the axons have regenerative potential. To assess the ability of a self-assembling peptide (SAP) nanofiber scaffold to facilitate the reconstruction of a tissue substrate that supports regeneration across the tissue disruption, brain wounds were inflicted in postnatal day-2 Syrian hamsters anesthetized by whole-body cooling. The scalp was opened and the OT within the SC was completely severed with a deep knife wound through a surgical opening in the cartilaginous skull, extending 1-2 mm below the surface from the midline to a point beyond the lateral margin of SC.

FIG. 2 is a parasaggital view of an adult hamster brain showing a schematic representation of the lesion (indicated with arrows) that transected the optic tract in the middle of the superior colliculus. FIG. 3 is a dorsal view reconstruction of the hamster brain with cortex removed. Rostral is to the right and caudal is to the left. The straight black line is the location of the transection of the optic tract made at postnatal day 2 (P2). Other areas of the brain shown include the superior colliculus (SC), pretectal area (PT), lateral posterior nucleus (LP), medial geniculate body (MGB), and inferior colliculus (IC).

Animals survived the procedure for 1, 3, 6, 30 or 60 days. At surgery, 10 animals were treated by injection into the brain wound of 10 ul of 1% SAP RADA16-I. Control animals with the same lesion included 3 with isotonic saline injection (10 ul), and 27 earlier cases with knife cuts and no injection, surviving 6-9 days. Additional animals were injected with SAP and the vital dye Congo Red at 1% solution, in an effort to determine whether Congo Red would stain the peptide structure (which it did not, under these conditions). The Congo Red inhibits cell growth, thus these injections served as an additional negative control. Initial experiments had shown that addition of the SAP to CSF in vitro resulted in self-assembly to form a peptide scaffold, confirming that CSF contains sufficient a concentration of ions to support self-assembly (data not shown).

Figure 4:
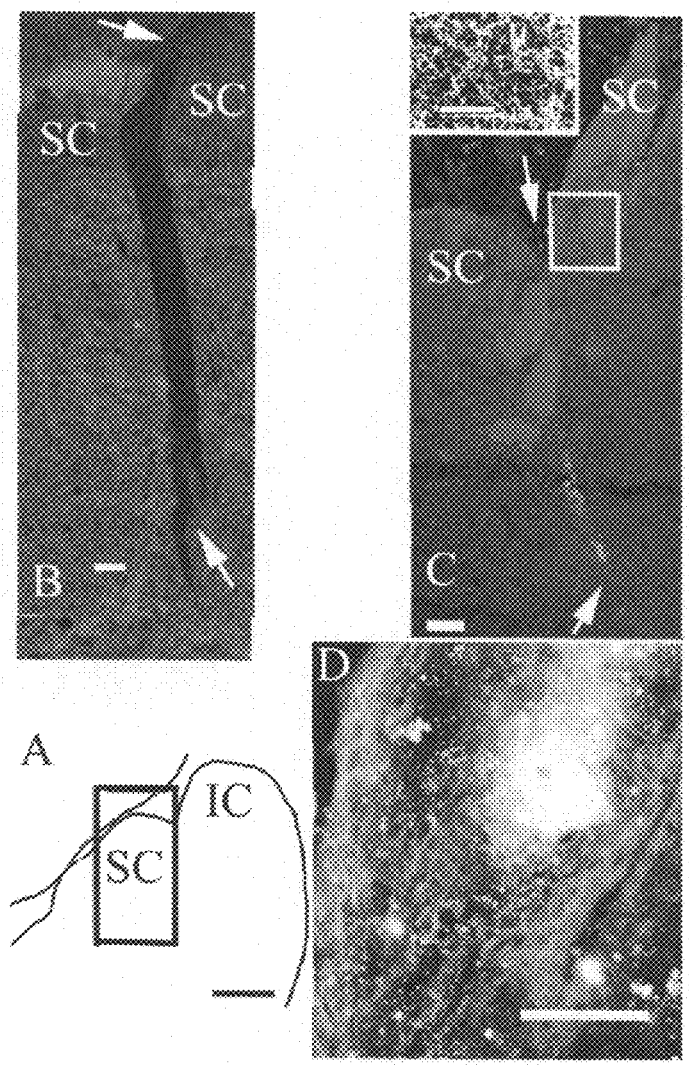
FIG. 4A is a schematic illustration of a parasagittal section of the dorsal midbrain of a hamster; rectangle is the approximate location of images 4A and 4B. Scale bar 500 microns.
FIG. 4B is an image showing a parasagittal section from the brain of a 1 month old hamster with a saline-injected lesion inflicted at day P2. Arrows show the path and extent of the knife cut.
FIG. 4C is an image showing a part of a section similar to that shown in FIG. 4B, from a 1 month hamster which had a lesion inflicted at day P2 that was injected with 10 microliters of 1% SAP RADA16-I. Retinal projections show as gray in this Figure. Scale bar 100 microns. The inset shows a SAP scaffold seen in much higher magnification (scale bar 1 micron), taken with a scanning electron microscope.
FIG. 4D shows an enlarged view of area indicated with the box in FIG. 4C. Regrown axons are seen in white. Scale bar 100 microns.

Histological results revealed that only in the animals treated with SAP alone, the tissue appears to have reconnected across the lesion at all survival times ($\chi^2$=34.8, df (1), p<<0.001). FIGS. 4-7 show representative results obtained at various times following infliction of the lesion. FIG. 4A shows a schematic illustration of a parasagittal section of the dorsal midbrain of a hamster, with the rectangle showing the approximate location of images presented in panels 4A and 4B. FIG. 4B shows a parasagittal section from the brain of a 1 month old hamster with a saline-injected lesion inflicted at day P2. Arrows show the path and extent of the knife cut. The longitudinal cavity shows the failure of the tissue to form a bridge or grow together at the site of the lesion. FIG. 4C is an image showing a part of a section similar to that shown in FIG. 4B, from a 1 month hamster which had a lesion inflicted at day P2 that was injected with 10 microliters of 1% SAP RADA16-I. Retinal projections show as gray. In contrast to the saline-injected control, the proximal and distal faces of the SAP-injected lesion are not separated by a large cavity and appear to have grown together. In addition, axons have extended from a location proximal to the lesion to a distal location. FIG. 4D shows an enlarged view of area indicated with the box in FIG. 4C. Regrown axons, traced with a standard choleratoxin labeling procedure using immunohistochemistry, are seen in white. The bright region in the upper right is an area of dense termination of axons that have crossed the lesion, seen with fluorescence microcopy.

Figure 5A:
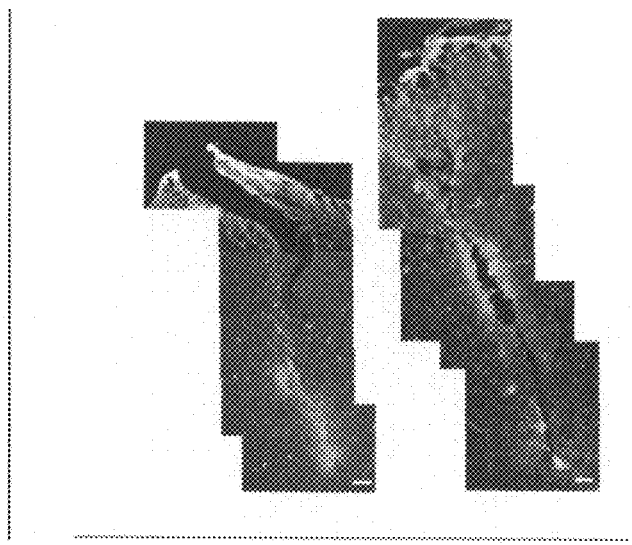
FIGS. 5A and 5B show images of parasaggital sections from animals sacrificed at 24 and 72 hours postlesion and injection of SAP.
Figure 5B:
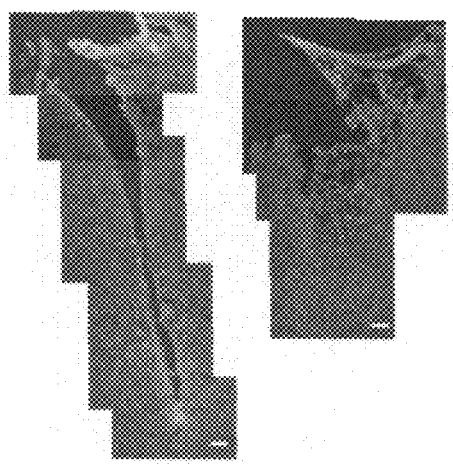
Figure 6A:
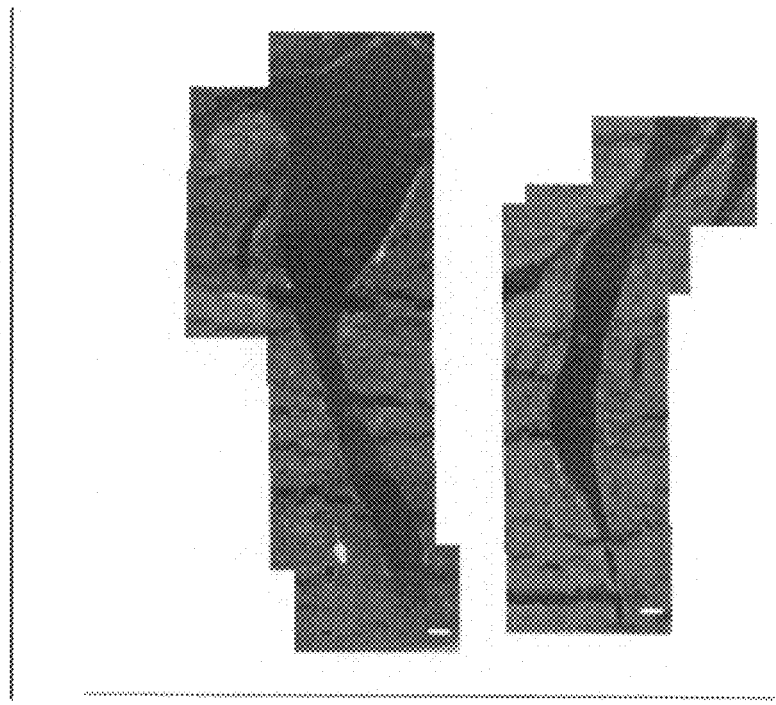
FIGS. 6A and 6B show images of parasaggital sections from animals one month postlesion and injection of SAP.
Figure 6B:
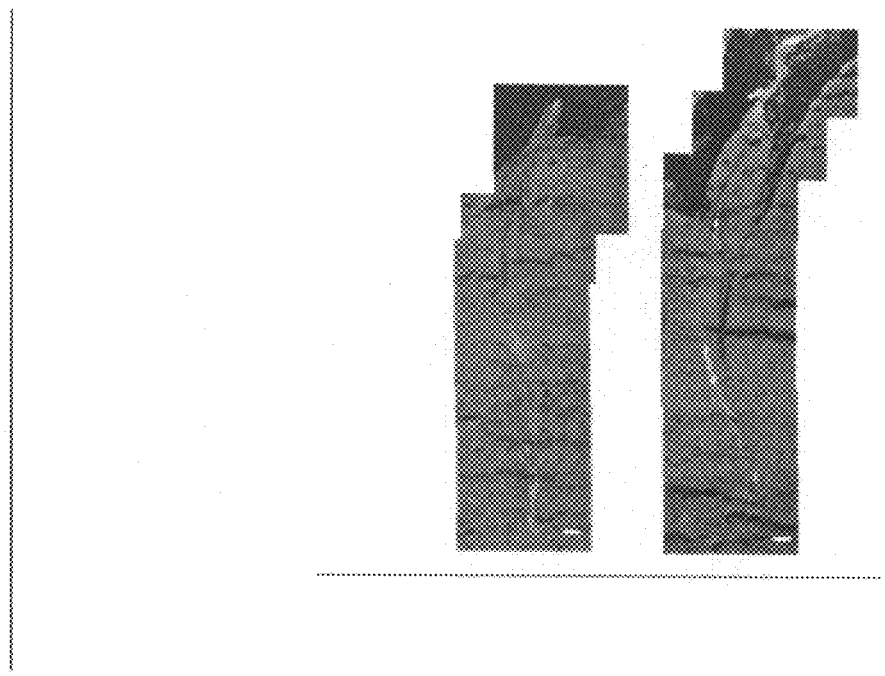
Figure 7A:
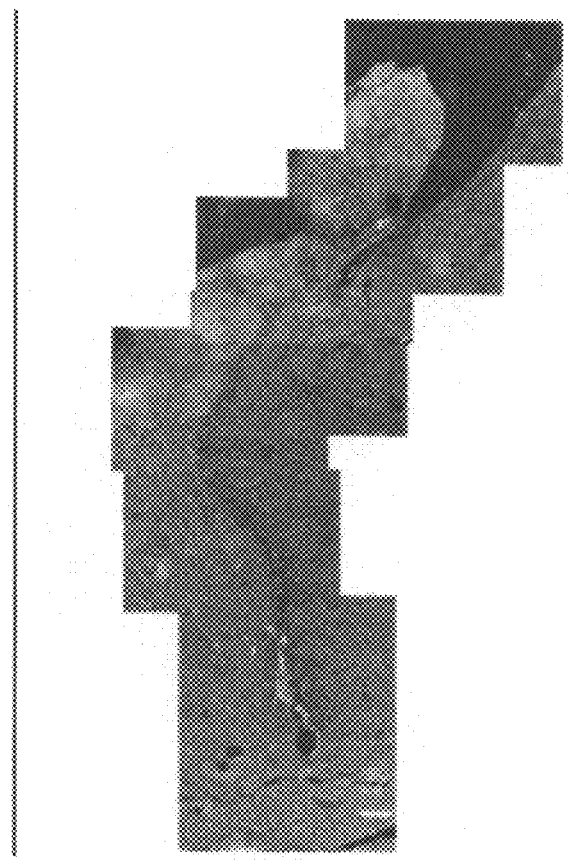
FIG. 7A shows a dark-field photo (composite) of a lesion site 2 months after infliction of the lesion and injection of SAP.
Figure 7B:
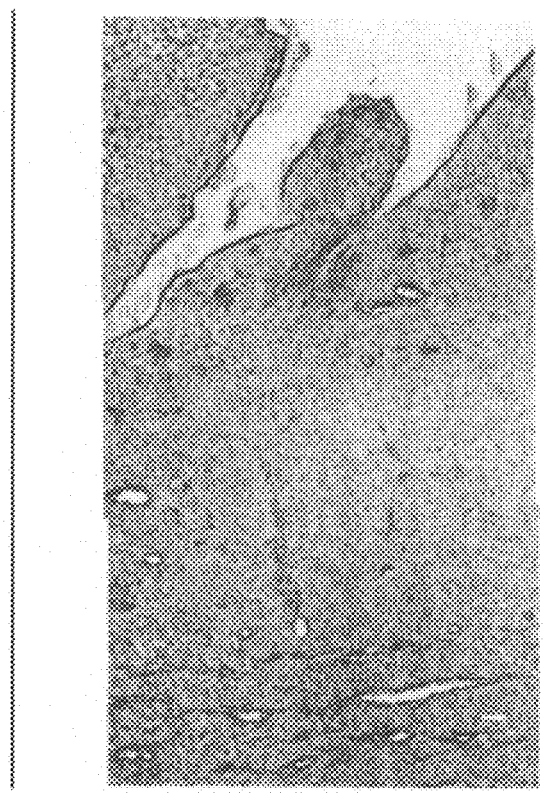
FIG. 7B is a corresponding bright-field image. Scale bars 100 microns.

FIGS. 5-7 show results obtained with SAP injection at additional time points following lesioning. FIG. 5 shows parasaggital sections from animals sacrificed at 24 and 72 hours postlesion and injection of SAP. 24 hour survival cases are shown in FIG. 5A. 72 hour survival cases are shown in FIG. 5B. In each panel, the image on the left shows lesions injected with SAP and Congo Red, while the image on the right shows lesions injected with SAP alone. FIG. 6 shows images of parasaggital sections from animals one month postlesion and injection of SAP. FIG. 6A shows images from two animals injected with SAP and Congo Red (similar to saline controls not shown). FIG. 6B shows images from two animals injected with SAP alone. FIG. 7A shows a dark-field photo (composite) of a lesion site 2 months after infliction of the lesion and injection of SAP. FIG. 7B is a corresponding bright-field image. Note the minimal nature of the scar in the bright field picture.

These results demonstrate that in the presence of the SAP peptide, tissue bridges the gap created by the lesion, and partial re-innervation of the caudal SC by the severed retinofugal axons can occur. Thus, the SAP is shown to offer a new means of ameliorating the tissue disruptions caused by injury to the CNS, allowing regrowth of axons that have regenerative potential.

Example 2

Introduction of a SAP at a Site of Injury Promotes Anatomic and Functional Recovery in Adult Hamsters We have previously demonstrated success using peripheral nerve autografts to bridge sites of transection of the optic tract, as assessed by behavioral recovery as well as by neuroanatomical tracing of the retinal projections [18]. Syrian hamsters are a good animal for such experiments because they become blind in tests of visually elicited head turning after complete severance of the brachium of the superior colliculus (BSC). Thus functional recovery of severed axons can be assessed by evaluating visually elicited head turning at various times after infliction of a lesion that severs the brachium, such as those described in Example 1.

To determine the extent of return of vision the animals are tested for visually elicited orienting responses [3, 51]. The identity of the animal is unknown to the investigator during testing periods. Before behavioral testing, the animals are habituated to the testing environment. Videotaping of the response is accomplished by the use of an overhead Sony digital video (DV) recorder. Some of the trials are simultaneously taped from the side with another Sony DV recorder. Later the video is analyzed frame-by-frame on a 21-inch monitor. All of the cameras are time synchronized. The first type of analysis is to determine if the trial is valid or invalid. Once a trial is judged as valid it is analyzed frame by frame, which enables us to plot the position of the stimulus with respect to the initial head location. The angle of the head at the beginning of the turning movement is set to zero. The angular position of the stimulus is plotted with reference to the initial head position. To plot the trajectory of the turn we plot the changing position of the head over time and in each frame we also plot the position of the stimulus. This insures that if the stimulus is moved during the trial we can see the true relative position of the stimulus with respect to the head at any moment. The data obtained from these analyses are converted into graphs of the elicited orienting movements. Leftward turns are plotted as positive on the y axis and rightward turns are plotted as negative values. Upon completion of testing the animals are prepared for histological procedures.

Figure 8:
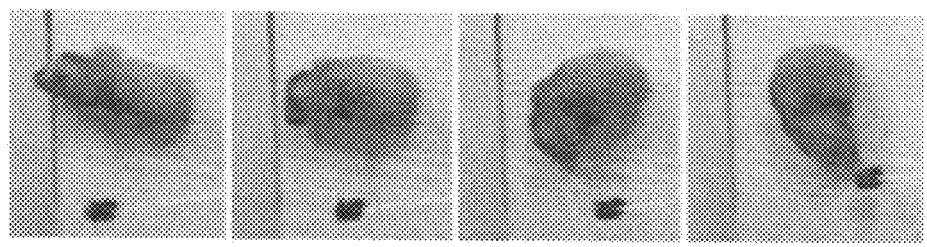
FIG. 8 shows frames from a videotape of an adult animal whose ability to respond to a visual stimulus following is being tested and quantified. The figure shows an animal that had been subjected to transection of the optic tract. Following transection of the optic tract, peripheral nerve (PN) bridges were surgically implanted to promote neural tissue regeneration. The animal turns toward the stimulus in the affected left visual field in small steps, prolonged here by movements of the stimulus away from him. Each frame is taken from a single turning movement, at times 0.00, 0.27, 0.53, and 0.80 sec from movement initiation. The animal reached the stimulus just after the last frame. This is about 0.20 sec slower than most turns by a normal animal and shows a return of functional vision after treatment. Similar results were obtained following treatment with SAP.

FIG. 8 shows that an adult animal, (with a transected optic tract after regeneration facilitated by surgically implanted PN bridges) turns toward the stimulus in the affected left visual field in small steps, prolonged here by movements of the stimulus away from him. Each frame is taken from a single turning movement, at times 0.00, 0.27, 0.53, and 0.80 sec from movement initiation. The animal reached the stimulus just after the last frame. This is about 0.20 sec slower than most turns by a normal animal.

The procedures described above were used to assess functional recovery in adult hamsters that had been subjected to deep transections of the brachium of the superior colliculus (BSC) in the midbrain at 2 months of age. In untreated animals, such transections can completely block the re-innervation of the superior colliculus (SC) by the retina. The lesion was located as shown in FIG. 9. At the time of surgery, animals were treated by injection of 10 ul of 1% SAP RAD16-I into the brain wound. Animals were allowed to recover from surgery and maintained under standard laboratory conditions.

The animals were subjected to behavioral testing beginning at day 44-46 after surgery. SAP treatment supported partial re-innervation of the SC by the severed retinofugal axons sufficient for significant behavioral recovery. Following SAP treatment neural tissue reconnected across the site of the lesion with axons growing through the site where the cut transected the brachium of the superior colliculus. Behavioral testing started at 44-46 days following infliction of the lesion and injection of SAP. Animals were tested by assessing their response when presented with a stimulus (a seed) that was brought into the visual field from the side. Normal animals turn toward the seed approximately 100% of the time.

Figure 12:
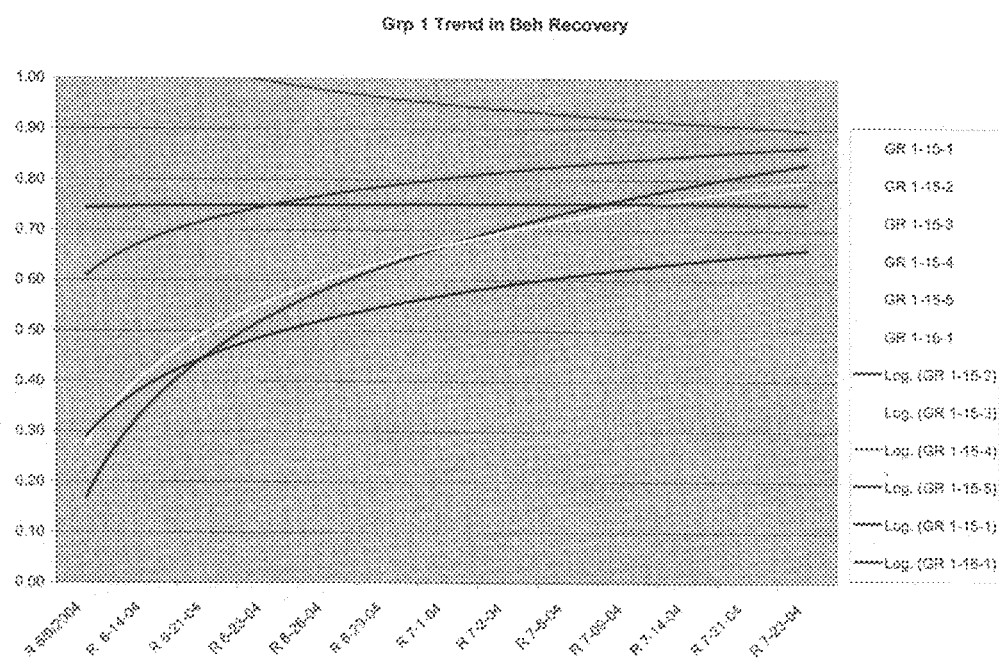
FIG. 12 shows behavioral data from six animals from behavioral tests that assessed the response of animals to a visual stimulus. The animals had been subjected to a lesion that transected the brachium of the SC at 2 months of age. The lesion was injected with 10 μl of 1% SAP RAD16-I at the time of surgery, and the animals were allowed to recover. Animals were tested by assessing their response when presented with a stimulus (a seed) that was brought into the visual field from the side. The x axis show the dates tested. The y-axis represents the number of times the animal turned toward the stimulus during testing, expressed as a percentage of the number of times the stimulus was presented on the side of the animal that was rendered blind by the lesion. An upward trend signifies improving vision while a downward trend would signify worsening vision. The dark blue line is the behavioral results of an adult animal the anatomical results for which are shown in FIG. 9. The aqua line is believed to represent an animal that experienced a rapid return of vision, which was complete prior to the start of behavioral testing.

Initial data demonstrates a return of functional vision in six animals, as shown in FIG. 12. The x axis in the figure shows the dates tested. The y axis represents the number of times the animal turned toward the stimulus during testing, expressed as a percentage of the number of times the stimulus was presented on the side that had received the lesion and SAP treatment. For example, a value of 0.5 represents turning towards the stimulus on 50% of the trials. Typically the stimulus was presented about 20 times on each side to avoid development of a turning preference. Trend lines representing the results of all trials on each day were plotted using the logarithmic trendline function of Microsoft Excel to calculate the least squares fit. An upward trend signifies improving vision while a downward trend would signify worsening vision. Note that the trend lines are up and to the right signifying return of vision over time after complete transection of the brachium of the SC and treatment with SAP. The dark blue line represents the behavioral results for an adult animal, the anatomical results for which are shown in FIG. 10. The aqua line is believed to represent an animal that experienced a rapid return of vision, which was complete prior to the start of behavioral testing.

Following the conclusion of behavioral testing, animals were subjected to intraocular injections of 1 µl of 1% Cholera-toxin subunit B (CT-B) conjugated with fluorescein isothiocyanate (CTB-FITC) (List Biological, Inc) into the vitreous humor of the right eye. Axon tracing and histology were performed as described above to allow visualization of the lesion site and assessment of axon regrowth. FIG. 10 is a parasagittal section of the dorsal midbrain of a hamster. Rostral is left and caudual is right. The section is from an 8 month old hamster and was taken 2 months following infliction of the lesion. The bright yellow in the middle of the picture that extends from the lower left to the upper right is in the middle of the lesion site. Retinal projections show as gray. Note the axons extending through the center of the cut. The area of densest crossing is in the upper right of the picture as seen with fluorescence microscopy, however there are axons along most of the site. In addition, the tissue has reconnected at the lesion site in a similar manner to that observed in the younger animals.

FIG. 11 is a parasagittal section of the dorsal midbrain of a hamster. Rostral is left and caudual is right. The section is from an 8 month old hamster and was taken 2 months following injection of 10 µl of 1% SAP RAD16-I into a lesion that transected the brachium of the SC. The lesion site extends from top of the picture to the bottom in the middle of the picture. White arrows indicate the middle of the lesion. Retinal projections show as gray. Note the axons extending through the center of the area where the cut was located. All of the tissue has repaired itself, and axons have extended their processes to the superior colliculus. The area of densest crossing is in the upper right of the picture as seen with fluorescence microscopy. The re-grown axons were traced with cholera-toxin fragment B labeling and using immunohistochemistry for amplification of the tracer. This figure was taken at lower magnification than FIG. 11 and thus shows healing of the lesion over a larger scale. The site of the cut is essentially indistinguishable from the surrounding unlesioned tissue.

The foregoing description is to be understood as being representative only and is not intended to be limiting. Alternative systems and techniques for making and using the compositions and devices of the invention and for practicing the inventive methods will be apparent to one of skill in the art and are intended to be included within the accompanying claims.

REFERENCES

1. Aguayo, A. J., et al., *Growth and connectivity of axotomized retinal neurons in adult rats with optic nerves substituted by PNS grafts linking the eye and the midbrain.* Ann NY Acad Sci, 1987. 495: p. 1-9.
2. Aguayo, A. J., et al., *Regrowth and connectivity of injured central nervous system axons in adult rodents.* Acta Neurobiol Exp, 1990. 50(4-5): p. 381-9.
3. So, K. F., G. E. Schneider, and S. Ayres, *Lesions of the brachium of the superior colliculus in neonate hamsters: correlation of anatomy with behavior.* Exp Neurol, 1981. 72(2): p. 379-400.
4. So, K. F. and A. J. Aguayo, *Lengthy regrowth of cut axons from ganglion cells after peripheral nerve transplantation into the retina of adult rats.* Brain Res, 1985. 328(2): p. 349-54.
5. Heiduschka, P. and S. Thanos, *Aurintricarboxylic acid promotes survival and regeneration of axotomised retinal ganglion cells in vivo.* Neuropharmacology, 2000. 39(5): p. 889-902.
6. Thanos, S. and J. Mey, *Type-specific stabilization and target-dependent survival of regenerating ganglion cells in the retina of adult rats.* J Neurosci, 1995. 15(2): p. 1057-79.

7. Thanos, S., *Neurobiology of the regenerating retina and its functional reconnection with the brain by means of peripheral nerve transplants in adult rats.* Surv Ophthalmol, 1997. 42 Suppl 1: p. S5-26.
8. Thanos, S., R. Naskar, and P. Heiduschka, *Regenerating ganglion cell axons in the adult rat establish retinofugal topography and restore visual function.* Exp Brain Res, 1997. 114(3): p. 483-91.
9. Sasaki, H., et al., *Light-dark discrimination after sciatic nerve transplantation to the sectioned optic nerve in adult hamsters.* Vision Res, 1993. 33(7): p. 877-80.
10. Fukuda, Y., et al., *Functional recovery of vision in regenerated optic nerve fibers.* Vision Res, 1998. 38(10): p. 1545-53.
11. Keirstead, S. A., et al., *Responses to light of retinal neurons regenerating axons into peripheral nerve grafts in the rat.* Brain Res, 1985. 359(1-2): p. 402-6.
12. Keirstead, S. A., et al., *Electrophysiologic responses in hamster superior colliculus evoked by regenerating retinal axons.* Science, 1989. 246(4927): p. 255-7.
13. Sauve, Y., H. Sawai, and M. Rasminsky, *Functional synaptic connections made by regenerated retinal ganglion cell axons in the superior colliculus of adult hamsters.* J Neurosci, 1995. 15(1 Pt 2): p. 665-75.
14. Sauve, Y., H. Sawai, and M. Rasminsky, *Topological Specificity in Reinnervation of the Superior Colliculus by Regenerated Retinal Ganglion Cell Axons in Adult Hamsters.* J Neurosci, 2001. 21(3): p. 951-960.
15. Carter, D. A., G. M. Bray, and A. J. Aguayo, *Regenerated retinal ganglion cell axons form normal numbers of boutons but fail to expand their arbors in the superior colliculus.* J Neurocytol, 1998. 27(3): p. 187-96.
16. Carter, D. A., G. M. Bray, and A. J. Aguayo, *Regenerated retinal ganglion cell axons can form well-differentiated synapses in the superior colliculus of adult hamsters.* J Neurosci, 1989. 9(11): p. 4042-50.
17. Ellis-Behnke, R., F. Khan, and G. E. Schneider. *A multifactor approach to the problem of obtaining functionally useful CNS axon regeneration.* in *The Second Asia Pacific Symposium on Neural Regeneration.* 2000. Xi'an, China.
18. Schneider, G. E., et al., *Visual function due to regeneration of optic nerve or optic tract through peripheral nervve homografts.* Abstracts, Soc. Neurosci., 2000. 26: p. 611.
19. Sawai, H., et al., *Functional and morphological restoration of intracranial brachial lesion of the retinocollicular pathway by peripheral nerve autografts in adult hamsters.* Exp Neurol, 1996. 137(1): p. 94-104.
20. Aleksandrova, M. A., et al., [*Effect of the foreign gene GDNF on development of homo- and xenografts in the rat brain*]. Genetika, 2000. 36(11): p. 1553-60.
21. Brundin, P., et al., *Intracerebral xenografts of dopamine neurons: the role of immunosuppression and the blood-brain barrier.* Exp Brain Res, 1989. 75(1): p. 195-207.
22. Kitchigina, V. F. and O. S. Vinogradova, *Functional integration of the rat hippocampal tissue, transplanted into the rabbit septum.* Brain Res, 1989.502(1): p. 39-52.
23. Korochkin, L. I., [*New approaches in developmental genetics and gene therapy: xenotransplantation of Drosophila embryonic nerve cells into the brain of vertebrate animals*]. Genetika, 2000. 36(11): p. 1436-42.
24. Larsson, L. C., et al., *Intrastriatal ventral mesencephalic xenografts of porcine tissue in rats: immune responses and functional effects.* Cell Transplant, 2000. 9(2): p. 261-72.
25. Nakashima, H., K. Kawamura, and I. Date, *Immunological reaction and blood-brain barrier in mouse-to-rat cross-species neural graft.* Brain Res, 1988. 475(2): p. 232-43.
26. Remy, S., et al., *Different mechanisms mediate the rejection of porcine neurons and endothelial cells transplanted into the rat brain.* Xenotransplantation, 2001. 8(2): p. 136-48.
27. Arutiunov, A. I. and N. Meskhiia, [*Plastic repair of defects in the dura mater*]. Vopr Neirokhir, 1972. 36(3): p. 3-9.
28. Khodzhaev, A. P., G. L. Mednik, and L. B. Sergeev, [*Healing of meningo-cerebral wounds with a combination of plastic repair and hydrocortisone therapy under clinical and experimental conditions*]. Vopr Neirokhir, 1976(4): p. 35-7.
29. Teng, Y. D., et al., *Functional recovery following traumatic spinal cord injury mediated by a unique polymer scaffold seeded with neural stem cells.* Proc Natl Acad Sci USA, 2002. 99(5): p. 3024-9.
30. Bernstein, J. J., M. R. Wells, and M. E. Bernstein, *Effect of puromycin treatment on the regeneration of hemisected and transected rat spinal cord.* J Neurocytol, 1978. 7(2): p. 215-28.
31. Plant, G. W., A. R. Harvey, and T. V. Chirila, *Axonal growth within poly (2-hydroxyethyl methacrylate) sponges infiltrated with Schwann cells and implanted into the lesioned rat optic tract.* Brain Res, 1995. 671(1): p. 119-30.
32. Holmes, T. C., et al., *Extensive neurite outgrowth and active synapse formation on self-assembling peptide scaffolds.* Proc Natl Acad Sci USA, 2000. 97(12): p. 6728-33.
33. Zhang, S., et al., *Spontaneous assembly of a self-complementary oligopeptide to form a stable macroscopic membrane.* Proc Natl Acad Sci USA, 1993. 90(8): p. 3334-8.
34. Zhang, S., et al., *Self-complementary oligopeptide matrices support mammalian cell attachment.* Biomaterials, 1995. 16(18): p. 1385-93.
35. Zhang, S., et al., *Zuotin, a putative Z-DNA binding protein in Saccharomyces cerevisiae.* Embo J, 1992. 11(10): p. 3787-96.
36. Kisiday, J., Jin, M., Kurz, B., Hung, H., Semino, C., Zhang, S., Grodzinsky, A. J. (2002) Self-assembling peptide hydrogel fosters chondrocyte extracellular matrix production and cell division: implications for cartilage tissue repair. *Proc. Natl. Acad. Sci. USA,* 99, 9996-10001.
37. Caplan, M. R., et al., *Self-assembly of a beta-sheet protein governed by relief of electrostatic repulsion relative to van der Waals attraction.* Biomacromolecules, 2000. 1(4): p. 627-31.
38. Caplan, M. R., Schwartzfarb, E. M, Zhang, S., Kamm, R. D., Lauffenburger, D. A. (2002a) Control of self-assembling oligopeptide matrix formation through systematic variation of amino acid sequence. *Biomaterials,* 23, 219-227.
39. Leon, E. J., et al., *Mechanical properties of a self-assembling oligopeptide matrix.* J Biomater Sci Polym Ed, 1998. 9(3): p. 297-312.
40. Marini, D., Zhang, S., Hwang, W., Lauffenburger, D. & Kamm, R., *Helical ribbon intermediates in the self-assembly of a beta-sheet peptide.* (Submitted). 2001.
41. Zhang, S., *Emerging biological materials through molecular self-assembly.* Applied Biochemistry and Biotechnology (in press), 2001.
42. del Rio, J. A., et al., *Proliferation and differentiation of glialfibrillary acidic protein-immunoreactive glial cells in organotypic slice cultures of rat hippocampus.* Neuroscience, 1991. 43(2-3): p. 335-47.
43. Stoppini, L., P. A. Buchs, and D. Muller, *A simple method for organotypic cultures of nervous tissue.* J Neurosci Methods, 1991. 37(2): p. 173-82.

44. Ling, C., Ellis-Behnke, R. G. and Schneider, G. E., *Regeneration of neonatal hamster optic tract: inhibitory factors appear before developmental onset of regenerative failure.* (In Process), 2001.

45. Chen, D. F., et al., *Bcl-2 promotes regeneration of severed axons in mammalian CNS.* Nature, 1997. 385(6615): p. 434-9.

46. Reinhardt, D., et al., *Mapping of nidogen binding sites for collagen type IV, heparan sulfate proteoglycan, and zinc.* J Biol Chem, 1993. 268(15): p. 10881-7.

47. Huang-Lee, L. L., J. H. Wu, and M. E. Nimni, *Effects of hyaluronan on collagen fibrillar matrix contraction by fibroblasts.* J Biomed Mater Res, 1994. 28(1): p. 123-32.

48. Rosenblat, G., et al., *Acylated ascorbate stimulates collagen synthesis in cultured human foreskin fibroblasts at lower doses than does ascorbic acid.* Connect Tissue Res, 1998. 37(3-4): p. 303-11.

49. Lodish, H., et al., *Molecular Cell Biology.* 3 ed. 1998, New York: Freeman & Co.

50. Zhang, S., et al., *Biological surface engineering: a simple system for cell pattern formation.* Biomaterials, 1999. 20(13): p. 1213-20.

51. Schneider, G. E., *Is it really better to have your brain lesion early? A revision of the "Kennard principle".* Neuropsychologia, 1979. 17(6): p. 557-83.

52. Ling, C., G. E. Schneider, and S. Jhaveri, *Target-specific morphology of retinal axon arbors in the adult hamster.* Vis Neurosci, 1998. 15(3): p. 559-79.

53. Mikkelsen, J. D., *Visualization of efferent retinal projections by immunohistochemical identification of cholera toxin subunit B.* Brain Res Bull, 1992. 28(4): p. 619-23.

54. Villegas-Perez, M. P., et al., *Influences of peripheral nerve grafts on the survival and regrowth of axotomized retinal ganglion cells in adult rats.* J Neurosci, 1988. 8(1): p. 265-80.

55. Aguayo, A. J., et al., *Effects of neurotrophins on the survival and regrowth of injured retinal neurons.* Ciba Found Symp, 1996. 196: p. 135-44.

56. Cohen, A., G. M. Bray, and A. J. Aguayo, *Neurotrophin-4/5 (NT-4/5) increases adult rat retinal ganglion cell survival and neurite outgrowth in vitro.* J Neurobiol, 1994. 25(8): p. 953-9.

57. Mansour-Robaey, S., et al., *Effects of ocular injury and administration of brain-derived neurotrophic factor on survival and regrowth of axotomized retinal ganglion cells.* Proc Natl Acad Sci USA, 1994. 91(5): p. 1632-6.

58. Yip, H. K. and K. F. So, *Axonal regeneration of retinal ganglion cells: effect of trophic factors.* Prog Retin Eye Res, 2000. 19(5): p. 559-75.

59. Cho, K. S., et al., *Ciliary neurotrophic factor promotes the regrowth capacity but not the survival of intraorbitally axotomized retinal ganglion cells in adult hamsters.* Neuroscience, 1999. 94(2): p. 623-8.

60. Yick, L. W., et al., *Peripheral nerve graft and neurotrophic factors enhance neuronal survival and expression of nitric oxide synthase in Clarke's nucleus after hemisection of the spinal cord in adult rat.* Exp Neurol, 1999. 159(1): p. 131-8.

61. Rende, M., et al., *Immunolocalization of ciliary neuronotrophic factor in adult rat sciatic nerve.* Glia, 1992. 5(1): p. 25-32.

62. Varon, S. S. and R. P. Bunge, *Trophic mechanisms in the peripheral nervous system.* Annu Rev Neurosci, 1978. 1: p. 327-61.

63. Varon, S., S. D. Skaper, and M. Manthorpe, *Trophic activities for dorsal root and sympathetic ganglionic neurons in media conditioned by Schwann and other peripheral cells.* Brain Res, 1981. 227(1): p. 73-87.

64. Lundborg, G., F. M. Longo, and S. Varon, *Nerve regeneration model and trophic factors in vivo.* Brain Res, 1982. 232(1): p. 157-61.

65. Esser, P., et al., *CD95 (Fas/APO-1) antibody-mediated apoptosis of human retinal pigment epithelial cells.* Biochem Biophys Res Commun, 1995. 213(3): p. 1026-34.

66. Jiang, S., et al., *Fas mediates apoptosis and oxidant-induced cell death in cultured hRPE cells.* Invest Ophthalmol Vis Sci, 2000. 41(3): p. 645-55.

67. Kaplan, H. J., et al., *Fas ligand (CD95 ligand) controls angiogenesis beneath the retina.* Nat Med, 1999. 5(3): p. 292-7.

68. Lambooij, A. C., et al., *Apoptosis is present in the primate macula at all ages.* Graefes Arch Clin Exp Ophthalmol, 2000. 238(6): p. 508-14.

69. Chen, D. F., S. Jhaveri, and G. E. Schneider, *Intrinsic changes in developing retinal neurons result in regenerative failure of their axons.* Proc Natl Acad Sci USA, 1995. 92(16): p. 7287-91.

70. Ellis-Behnke, R., *A multifactor approach to the the problem of obtaining functionally useful CNS axon regeneration*, in *Brain and Gognitive Department*. 2002, Massachusetts Institute of Technology: Cambridge. p. 378.

71. Chen, R. W. and D. M. Chuang, *Long term lithium treatment suppresses p53 and Bax expression but increases Bcl-2 expression. A prominent role in neuroprotection against excitotoxicity.* J Biol Chem, 1999. 274(10): p. 6039-42.

72. Manji, H. K., G. J. Moore, and G. Chen, *Lithium at 50: have the neuroprotective effects of this unique cation been overlooked?* Biol Psychiatry, 1999. 46(7): p. 929-40.

73. Manji, H. K., G. J. Moore, and G. Chen, *Lithium up-regulates the cytoprotective protein Bcl-2 in the CNS in vivo: a role for neurotrophic and neuroprotective effects in manic depressive illness.* J Clin Psychiatry, 2000. 61(Suppl 9): p. 82-96.

74. Moore, G. J., et al., *Lithium increases N-acetyl-aspartate in the human brain: in vivo evidence in support of bcl-2's neurotrophic effects?* Biol Psychiatry, 2000. 48(1): p. 1-8.

75. Stichel, C. C., et al., *Inhibition of collagen IV deposition promotes regeneration of injured CNS axons.* Eur J Neurosci, 1999. 11(2): p. 632-46.

76. Ellis-Behnke, R. and G. E. Schneider. *In-vitro assay of CNS regeneration through lesion scars produced in-vivo, with treatments to increase growth.* in *Society for Neuroscience*. 2002.

77. Snow, D. M., et al., *Sulfated proteoglycans in astroglial barriers inhibit neurite outgrowth in vitro.* Exp Neurol, 1990. 109(1): p. 111-30.

78. Snow, D. M., et al., *A chondroitin sulfate proteoglycan may influence the direction of retinal ganglion cell outgrowth.* Development, 1991. 113(4): p. 1473-85.

79. Bomze, H. M., et al., *Spinal axon regeneration evoked by replacing two growth cone proteins in adult neurons.* Nat Neurosci, 2001. 4(1): p. 38-43.

80. Ellis-Behnke, R. and G. E. Schneider. *A method for non-viral genetic transfection in the CNS, using Bcl-2 in-vivo.* in *Society for Neuroscience.* 2001.

81. Mao, C., et al., *A nanomechanical device based on the B-Z transition of DNA.* Nature, 1999. 397(6715): p. 144-6.

82. Vogel, J., et al., *The role of glycolipids in mediating cell adhesion: a flow chamber study.* Biochim Biophys Acta, 1998. 1372(2): p. 205-15.

83. Archibald S. J., J. Shefner, C. Krarup, and R. D. Madison, *Monkey median nerve repaired by nerve graft or collagen nerve guide tube*. J. Neurosci., 1995. 15(5): 4109-4123.
84. DeVivo, M. J., *Epidemiology of traumatic spinal cord injury*, in Kischblum, S., Campagnolo, D. I., DeLlisa, J. A. (eds.) Spinal Cord Medicine, 2002. Lippincott Williams & Wilkins, Philadelphia, pp. 69-81.
85. Muntner, P., Garrett, E., Klag, M. J., and Coresh, J., *Trends in stroke prevalence between 1973 and 1991 in the US population 27 to 74 years of age*, Stroke, 2002. 33: 1209-1213.
86. Schmidt, C. E. and Leach, J. B., *Neural tissue engineering: strategies for repair and regeneration*. Annu. Rev. Biomed. Eng., 2003. 5: 293-347.
87. Lendahl, U., et al., *CNS stem cells express a new class of intermediate filament protein*, Cell, 60:585-595, 1990.
88. Samat, H., et al., *Neuronal nuclear antigen (NeuN): a marker of neuronal maturation in early human fetal nervous system*, Brain Research, 20:88-94, 1998.
89. Han, S.-O., R. I. Mahato, Y. K. Sung, and S. W. Kim. 2000. Development of Biomaterials for gene therapy. *Mol. Therapy* 2:302-317.
90. Thomas, N., and Klibanov, A. M. Non-viral gene therapy: polycation-mediated DNA delivery. *Appl. Microbiol. Biotechnol.* 62:27-34 (2003).
91. Berry, M., Barrett, L., Seymour, L., Baird, A., Logan, A., 2001. *Gene therapy for central nervous system repair*, Curr. Opin. Mol. Ther. 3: 338-49.
92. McManus, M. T., and P. A. Sharp. 2002. Gene silencing in mammals by short interfering RNAs. *Nature Rev. Gene.* 3:737-747.
93. Brummelkamp, T. R., R. Bernards, and R. Agami. 2002. A system for stable expression of short interfering RNAs in mammalian cells. *Science* 296:550-553.
94. Paddison, P. J., A. A. Caudy, E. Bernstein, G. J. Hannon, and D. S. Conklin. 2002. Short hairpin RNAs (shRNAs) induce sequence-specific silencing in mammalian cells. *Genes Dev.* 16:948-958.
95. McCaffrey, A. P., Nakai, H., Pandey, K., Huang, Z., Salazar, F. H., Xu, H., Wieland, S. F., Marion, P. L., and Kay, M. A. (2003). Inhibition of hepatitis B virus in mice by RNA interference. Nat Biotechnol 21, 639-644.
96. Bernstein S L, Guo Y, Kelman S E, Flower R W, Johnson M A., *Functional and cellular responses in a novel rodent model of anterior ischemic optic neuropathy*. Invest Ophthalmol Vis Sci. 2003 October; 44(10):4153-62.
97. Krueger K, Busch E. *Protocol of a thromboembolic stroke model in the rat: review of the experimental procedure and comparison of models*. Invest Radiol. 2002. 37(11):600-8.
98. Bjorklund A, Dunnett S B, Brundin P, Stoessl A J, Freed C R, Breeze R E, Levivier M, Peschanski M, Studer L, Barker R., *Neural transplantation for the treatment of Parkinson's disease.*, Lancet Neurol. 2003 July; 2(7):437-45.
99. Saarma, M. and H. Sariola, *Other neurotrophic factors: glial cell line-derived neurotrophic factor (GDNF)*. Microsc Res Tech, 1999. 45(4-5): p. 292-302.
100. Kotzbauer, P. T., et al., *Neurturin, a relative of glial-cell-line-derived neurotrophic factor*. Nature, 1996. 384(6608): p. 467-70.
101. Caplan, M. R., Schwartzfarb, E. M., Zhang, S., Kamm, R. D., Lauffenburger, D. A. (2002b) Effects of systematic variation of aminoacid sequence on the mechanical properties of a self-assembling, oligopeptide biomaterial. *J. Biomater. Sci. Polymer Edition*, 13, 225-236.

We claim:

1. A composition comprising:
   a nanoscale structured material comprising, self-assembling RADA 16-I (SEQ ID NO. 1) peptides provided at a concentration of between 0.1% (1 mg/ml) and 10% (100 mg/ml), inclusive, wherein the peptides are amphiphilic peptides that comprise substantially equal proportions of hydrophobic and hydrophilic amino acids and are complementary and structurally compatible, and wherein the nanoscale structured material provides an environment that is permissive for the repair of neural axons,
   one or more regeneration promoting factors; and
   an siRNA, shRNA, or a template for synthesis of an siRNA or shRNA that is targeted to a transcript that encodes the molecule that inhibits regeneration or repair.

2. The composition of claim 1, wherein the peptides self-assemble into a macroscopic structure.

3. The composition of claim 1, wherein the peptides are in solution.

4. The composition of claim 1, wherein the peptides are provided at a concentration of between 0.5% (5 mg/ml) and 5% (50 mg/ml), inclusive.

5. The composition of claim 1, wherein the peptides are provided at a concentration of approximately 5 mg/ml, approximately 10 mg/ml, approximately 15 mg/ml, or approximately 20 mg/ml.

6. The composition of claim 2, wherein the peptides self-assemble into a beta-sheet macroscopic structure.

7. The composition of claim 1, wherein the composition allows axon growth from a location on one side of an injury or barrier to a location on the other side of the site of injury or barrier.

8. The composition of claim 1, wherein the material or composition comprises a biologically active substance.

9. The composition of claim 1, wherein the material or composition comprises one or more regeneration promoting factor(s).

10. The composition of claim 9, wherein the one or more regeneration promoting factor(s) are selected from the group consisting of: nerve growth factor (NGF), brain derived neurotrophic factor (BDNF), neurotrophin-3 (NT-3), neurotrophin-4/5 (Nt-4/5), ciliary neurotrophic factor (CNTF), glial cell derived growth factor (GDNF), neurturin (NTN), persephin (PSP), artemin (ART), acidic fibroblast growth factor (aFGF), basic fibroblast growth factor (bFGF), growth-associated protein 43 (GAP-43), cytoskeleton-associated protein 23 (CAP-23), B-cell lymphoma 2 (Bcl-2), L1, neural cell adhesion molecule (NCAM), N-cadherin, agrin, laminin, acetylcholine receptor inducing activity protein (ARIA), a semaphorin, a slit protein, a netrin, and an ephrin.

* * * * *